United States Patent [19]
Ishida et al.

[11] Patent Number: 5,808,065
[45] Date of Patent: Sep. 15, 1998

[54] PYRIDAZINONE DERIVATIVES AND PROCESSES FOR PREPARING THE SAME

[75] Inventors: Akihiko Ishida, Urawa; Harutami Yamada, Hasuda; Michihisa Yato, Urawa; Shinsuke Nishiyama, Ohmiya; Fumikazu Okumura, Saitama-ken, all of Japan

[73] Assignee: Tanabe Seiyaku Co., Ltd., Osaka, Japan

[21] Appl. No.: 917,113

[22] Filed: Aug. 25, 1997

Related U.S. Application Data

[62] Division of Ser. No. 671,485, Jun. 27, 1996, Pat. No. 5,698,554.

[30] Foreign Application Priority Data

Jun. 27, 1995 [JP] Japan ................................. 7-160620
Feb. 6, 1996 [JP] Japan ................................. 8-19859

[51] Int. Cl.$^6$ ..................... C07D 237/30; C07D 401/00; C07D 403/00; C07D 405/00
[52] U.S. Cl. .......................... 544/235; 544/239
[58] Field of Search ..................... 544/235, 239

[56] References Cited

U.S. PATENT DOCUMENTS

| | | | |
|---|---|---|---|
| 4,820,705 | 4/1989 | Nickl et al. | 514/247 |
| 4,921,856 | 5/1990 | Schickaneder et al. | 514/252 |
| 5,409,956 | 4/1995 | Yoshida et al. | 514/562 |

FOREIGN PATENT DOCUMENTS

| | | |
|---|---|---|
| 0194548 | 9/1986 | European Pat. Off. |
| 0579059 | 1/1994 | European Pat. Off. |
| 0661273 | 7/1995 | European Pat. Off. |
| 0661274 | 7/1995 | European Pat. Off. |
| 53-124279 | 10/1978 | Japan |
| 63-145272 | 6/1988 | Japan |

*Primary Examiner*—Mukund J. Shah
*Assistant Examiner*—Bruck Kifle
*Attorney, Agent, or Firm*—Birch, Stewart, Kolasch & Birch, LLP

[57] ABSTRACT

Disclosed is a pyridazinone compound represented by the formula (I):

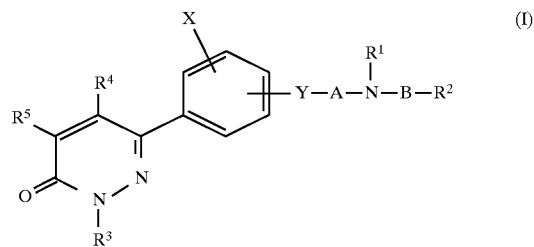

wherein X represents hydrogen atom or the like; Y represents a single bonding arm, oxygen atom or sulfur atom; A represents a straight or branched alkylene group which may have a double bond;

B represents carbonyl group or thiocarbonyl group; and $R^2$ represents an alkyl group having 1 to 10 carbon atoms which may be substituted or the like; or B represents sulfonyl group; and $R^2$ represents a lower alkenyl group or the like;

$R^1$ represents hydrogen atom or the like; $R^3$ represents hydrogen atom or the like; $R^4$ represents hydrogen atom or the like; and $R^5$ represents hydrogen atom or the like, or a pharmaceutically acceptable salt thereof.

1 Claim, No Drawings

PYRIDAZINONE DERIVATIVES AND PROCESSES FOR PREPARING THE SAME

This is a divisional of application Ser. No. 08/671,485, filed on Jun. 27, 1996 now U.S. Pat. No. 5,698,554, the entire contents of which are hereby incorporated by reference.

BACKGROUND OF THE INVENTION

This invention relates to novel pyridazinone derivatives having actions of treating nephritis and/or actions of protecting from endotoxin shock, and processes for preparing the same.

In Japanese Provisional Patent Publication No. 23853/1988, it has been disclosed that benzenesulfonamidindanyl compounds such as 6-(2-benzenesulfonamidindan-5-yl)-4,5-dihydropyridazin-3(2H)-one exhibit antithrombotic actions. Further, in PCT Patent Publication No. WO 92/15558, it has been disclosed that benzenesulfonaii-noalkylindane derivatives such as 6-[2-[(4-chlorophenyl)sulfonylaminomethyl]-indan-5-yl]-4,5-dihydropyridazin-3(2H)-one have thromboxane $A_2$ antagonistic actions.

In Japanese Provisional Patent Publication No. 124279/1978, it has been disclosed that pyridinaminoalkylphenyl derivatives such as 5-methyl-6-(4-[2-(pyridin-3-ylcarbonylamino)ethyl]phenyl)-4,5-dihydropyridazin-3(2H)-one have antiallergic actions. Further, in Japanese Provisional Patent Publication No. 212552/1986, it has been disclosed that benzenesulfonylaminophenyl derivatives such as 6-(4-[2-phenylsulfonylaminoethyl]phenyl)pyridazin-3(2H)-one have antithrombotic activities.

On the other hand, as an agent for treating endotoxin shock which occurs in a patient seriously infected with gram-negative bacteria, there have been conventionally used steroid hormones, aprotinin (a protease inhibitor) and dobutamine (a cardiac).

Further, as an agent for treating nephritis, there have been conventionally used prednisolon (a steroid agent), cyclophosphamide (an immunosuppressant), dipyridamole, dilazep (an antiplatelet agent) and heparin (an anticoagulant).

SUMMARY OF THE INVENTION

An object of the present invention is to provide novel pyridazinone derivatives having excellent actions of treating nephritis and/or excellent actions of protecting from endotoxin shock and having less side effect to a circulatory system, and processes for preparing the same.

That is, the present invention relates to a pyridazinone derivative represented by the formula (I):

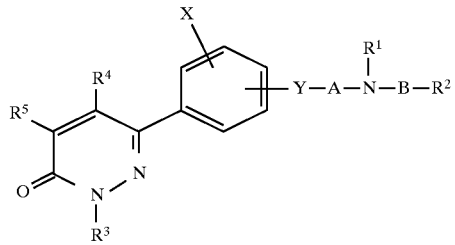

wherein X represents hydrogen atom, a lower alkyl group which may have a substituent(s), a lower alkoxy group, carboxy group, an alkoxycarbonyl group, nitro group, cyano group, a lower alkylthio group, hydroxy group, an amino group which may have a substituent(s), or a halogen atom; Y represents a single bonding arm, oxygen atom or sulfur atom; A represents a straight or branched alkylene group which may have a double bond;

B and $R^2$ each represent that

B represents carbonyl group or thiocarbonyl group; and $R^2$ represents an alkyl group having 1 to 10 carbon atoms which may be substituted, a cycloalkyl group having 3 to 6 carbon atoms, a lower alkenyl group, a phenyl-substituted lower alkenyl group, a lower alkoxy group which may have a substituent(s), phenoxy group, a lower alkylamino group, a lower alkenylamino group, phenylamino group, a lower alkenyloxy group, a monocyclic or bicyclic heterocyclic aromatic group which has at least one of nitrogen atom, oxygen atom and sulfur atom as a hetero atom(s) and may have a substituent(s), or an aryl group which may have a substituent(s); or B represents sulfonyl group; and $R^2$ represents an alkyl group having 1 to 10 carbon atoms which may be substituted, a cycloalkyl group having 3 to 6 carbon atoms, a lower alkenyl group, a phenyl-substituted lower alkenyl group or a monocyclic or bicyclic heterocyclic aromatic group which has at least one of nitrogen atom, oxygen atom and sulfur atom as a hetero atom(s) and may have a substituent(s);

$R^1$ represents hydrogen atom, a lower alkyl group which may be substituted or a lower alkenyl group; $R^3$ represents hydrogen atom or a lower alkyl group which may be substituted; $R^4$ represents hydrogen atom or a lower alkyl group; and $R^5$ represents hydrogen atom or a lower alkyl group, or a pharmaceutically acceptable salt thereof, and a process for preparing the same.

DESCRIPTION OF THE PREFERRED EMBODIMENTS

In the following, the present invention is explained in detail.

X in the formula (I) represents hydrogen atom; a lower alkyl group which may be substituted, preferably having 1 to 6 carbon atoms, more preferably 1 to 4 carbon atoms, particularly preferably 1 to 3 carbon atoms; a lower alkoxy group preferably having 1 to 6 carbon atoms, more preferably 1 to 4 carbon atoms, particularly preferably 1 to 3 carbon atoms; carboxy group; a lower alkoxycarbonyl group preferably having 2 to 7 carbon atoms, more preferably 2 to 5 carbon atoms, particularly preferably 2 to 4 carbon atoms; nitro group; cyano group; a lower alkylthio group preferably having 1 to 6 carbon atoms, more preferably 1 to 4 carbon atoms, particularly preferably 1 to 3 carbon atoms; hydroxy group; an amino group which may be substituted; or a halogen atom such as chlorine, bromine, iodine and fluorine. As the substituents for the alkyl group which may be substituted, there may be mentioned a halogen atom; a lower alkoxy group; an amino group which may be substituted by a mono- or di-lower alkyl group, or an acyl group; or a lower alkylthio group. As the substituents for the amino group, there may be mentioned a lower alkyl group, an acyl group, a lower alkoxycarbonyl group, carbamoyl group, thiocarbamoyl group (the nitrogen atom of said carbamoyl group or thiocarbamoyl group may be further substituted by 1 or 2 lower alkyl groups) and a lower alkylcarbamoyl group, and further the substituted amino group includes an amino group in which the ends of two substituents on the nitrogen atom are bonded to form a cyclic structure, such as pyrrolidino group, piperidino group, perhydroazepin-1-yl group, morpholino group, thiomorpholino group and piperazino group (the nitrogen atom at 4-position of said piperazino group may be further substituted by a lower alkyl group, a lower alkenyl group, an acyl group, an aryl group or the like).

Y in the formula (I) represents a single bonding arm; oxygen atom or a sulfur atom; preferably a single bonding arm.

A in the formula (I) represents a straight or branched alkylene group which may have a double bond, preferably those having 1 to 10 carbon atoms, more preferably 2 to 10 carbon atoms, particularly preferably 2 to 6 carbon atoms. As a specific example thereof, there may be mentioned methylene group, ethylene group, trimethylene group, tetramethylene group, pentamethylene group, hexamethylene group, heptamethylene group, octamethylene group, non-amethylene group, 2-methyltetramethylene group, 2-ethyltetramethylene group and 1-butenylene group (the number showing the position of a branched chain or a double bond is to be counted from a carbon atom at the side of a partial structure Y being bonded in the formula (I); hereinafter the same), preferably methylene group, ethylene group, trimethylene group, tetramethylene group, pentamethylene group, hexamethylene group, 2-methyltetramethylene group and 2-ethyltetramethylene group.

B in the formula (I) represents carbonyl group, thiocarbonyl group or sulfonyl group. When B represents carbonyl group or thiocarbonyl group, $R^2$ in the formula (I) represents an alkyl group having 1 to 10 carbon atoms which may be substituted, preferably having 1 to 6 carbon atoms, more preferably 1 to 4 carbon atoms; a cycloalkyl group having 3 to 6 carbon atoms; a lower alkenyl group preferably having 2 to 7 carbon atoms, more preferably 2 to 5 carbon atoms; a phenyl-substituted lower alkenyl group preferably having 2 to 7 alkenyl carbon atoms, more preferably 2 to 5 alkenyl carbon atoms; a lower alkoxy group which may have a substituent, preferably having 1 to 6 carbon atoms, more preferably 1 to 4 carbon atoms; phenoxy group; a lower alkylamino group preferably having 1 to 6 carbon atoms, more preferably 1 to 4 carbon atoms; a lower alkenylamino group preferably having 2 to 7 carbon atoms, more preferably 2 to 5 carbon atoms; phenylamino group; a lower alkenyloxy group preferably having 2 to 7 carbon atoms, more preferably 2 to 5 carbon atoms; a monocyclic or bicyclic heterocyclic aromatic group which has at least one hetero atom selected from nitrogen atom, oxygen atom and sulfur atom and may be substituted; or an aryl group which may be substituted. When B represents sulfonyl group, $R^2$ represents an alkyl group having 1 to 10 carbon atoms which may be substituted, preferably having 1 to 6 carbon atoms, more preferably 1 to 4 carbon atoms; a cycloalkyl group having 3 to 6 carbon atoms; a lower alkenyl group preferably having 2 to 7 carbon atoms, more preferably 2 to 5 carbon atoms; a phenyl-substituted lower alkenyl group preferably having 2 to 7 alkenyl carbon atoms, more preferably 2 to 5 alkenyl carbon atoms; or a monocyclic or bicyclic heterocyclic aromatic group which has at least one hetero atom selected from nitrogen atom, oxygen atom and sulfur atom and may be substituted.

In $R^2$, as the substituents for the alkyl group, there may be mentioned a halogen atom; a lower alkoxy group; an amino group which may be substituted by a mono- or di-alkyl group, or a lower acyl group; or a lower alkylthio group.

As the phenyl-substituted lower alkenyl group, there may be mentioned, for example, styryl group. As the lower alkoxy group which may have a substituent, there may be mentioned, for example, a lower alkoxy group which may be substituted by phenyl group. As the monocyclic or bicyclic heterocyclic aromatic group which has at least one of nitrogen atom, oxygen atom and sulfur atom as a hetero atom(s) and may have a substituent(s) (e.g., a pyridyl group, furyl group, thienyl group, pyrazinyl group, pyrimidinyl group, pyridazinyl group, pyrrolyl group, imidazolyl group, pyrazolyl group, quinolyl group, isoquinolyl group, indolyl group, isoindolyl group, thiazolyl group, isoxazolyl group, oxazolyl group, quinazolinyl group, thienopyrimidinyl group, triazinyl group, tetrazolyl group, quinoxalinyl group, benzothienyl group, benzothiazolyl group, benzoxazolyl group, benzoimidazolyl group, isothiazolyl group, phthalazinyl group or benzofuryl group each of which may be substituted by 1 to 4 substituents selected from the group consisting of a lower alkyl group, a halogeno-lower alkyl group, a lower alkoxy group, a lower alkylthio group, hydroxy group, mercapto group, cyano group, amino group, a mono-lower alkylamino group, a di-lower alkylamino group, an acylamino group, a halogen atom, phenoxy group, carboxy group, a lower alkoxycarbonyl group, a lower alkylcarbonyloxy group, a lower alkylcarbonyl group, carbamoyl group, a mono-lower alkylcarbamoyl group and a di-lower alkylcarbamoyl group. As the aryl group which may have a substituent(s), there may be mentioned, for example, a phenyl group which may be substituted by 1 to 3 substituents selected from the group consisting of a lower alkoxy group, a phenyl-substituted lower alkoxy group, a halogen atom, hydroxy group, trifluoromethyl group, nitro group, a lower alkyl group and a di-lower alkylamino group.

$R^1$ in the formula (I) represents hydrogen atom; a lower alkyl group which may be substituted, preferably having 1 to 6 carbon atoms, more preferably 1 to 4 carbon atoms, particularly preferably 1 to 3 carbon atoms; or a lower alkenyl group preferably having 2 to 7 carbon atoms, more preferably 2 to 5 carbon atoms. As the substituents for the alkyl group, there may be mentioned phenyl group, pyridyl group, furyl group, thienyl group and pyrazinyl group.

$R^3$ in the formula (I) represents hydrogen atom or a lower alkyl group which may be substituted, preferably having 1 to 6 carbon atoms, more preferably 1 to 4 carbon atoms, particularly preferably 1 to 3 carbon atoms. As the substituents for the alkyl group, there may be mentioned cyano group, amino group which may be substituted, an alkylcarbamoyl group, an alkoxycarbonyl group, hydroxycarbonyl group, phenyl group which may be substituted, pyridyl group, furyl group, thienyl group, pyrazinyl group, tetrazolyl group or piperazinyl group.

As the amino group which may be substituted, those as mentioned above for X may be mentioned.

As the phenyl group which may be substituted, those as mentioned above for $R^2$ may be mentioned.

$R^4$ and $R^5$ in the formula (I) each represent hydrogen atom or a lower alkyl group preferably having 1 to 6 carbon atoms, more preferably 1 to 4 carbon atoms, particularly preferably 1 to 3 carbon atoms.

Among the desired compounds (I) of the present invention, as an example of a preferred compound group, there may be mentioned, for example, a group comprising compounds having at least one of the following characteristics:

(a): X is hydrogen atom,
(b): Y is a single bonding arm,
(c1): A is a straight or branched alkylene group which may have a double bond, having 2 to 10 carbon atoms,
(c2): A is a straight or branched alkylene group having 2 to 6 carbon atoms, (d1): B is carbonyl group,
(d2): B is sulfonyl group,
(e1): $R^2$ is a pyridyl group which may have 1 or 2 substituents selected from the group consisting of a lower alkyl group, a halogeno-lower alkyl group, a lower alkoxy group, a lower alkylthio group, hydroxy group, mercapto group, cyano group, amino group, a substituted amino group, a halogen atom, phenoxy group, carboxy group, a lower alkoxycarbonyl group, a lower alkylcarbonyloxy group, a lower alkylcarbonyl group, carbamoyl group, a mono-lower alkylcarbamoyl group and a di-lower alkylcarbamoyl group; a lower alkyl group; or a lower alkenyl group, more preferably,
(e2): $R^2$ is a pyridyl group which may have 1 or 2 substituents selected from the group consisting of a lower alkyl group, a lower alkylamino group and amino group; a lower alkyl group; or a lower alkenyl group,
(e3): $R^2$ is a lower alkyl group or a lower alkenyl group, more preferably, (e4): $R^2$ is vinyl group or a lower alkyl group,
(e5): $R^2$ is a pyridyl group which may optionally be substituted by one or two member selected from a lower alkyl group, a lower alkylamino group and an amino group,
(f): $R^3$ is hydrogen atom,
(g): $R^4$ is hydrogen atom, and
(h): $R^5$ is hydrogen atom.

As an example of a more preferred compound group, there may be mentioned, for example, a group comprising compounds having the following characteristics:

(d1) and (e1), or (d2) and (e3).

As an example of a further preferred compound group, there may be mentioned, for example, a group comprising compounds having the following characteristics:

(d1) and (e5), or (d2) and (e4).

As an example of a particularly preferred compound group, there may be mentioned, for example, a group comprising compounds having the following characteristics:

(b), (c1), (d1), (e1), (f), (g) and (h), or
(b), (c1), (d2), (e3), (f), (g) and (h).

As an example of the most preferred compound group, there may be mentioned, for example, a group comprising compounds having the following characteristics:

(b), (c2), (d1), (e5), (f), (g) and (h), or
(b), (c2), (d2), (e4), (f), (g) and (h).

In "the pyridyl group which may have a substituent(s)" of $R^2$, the substitution position of the substituent on the pyridine ring and the position at which the partial structure: —B— is bonded are not particularly limited, but as a preferred example, there may be mentioned a pyridyl group which is bonded by the partial structure: —B— at 3-position on the pyridine ring, i.e., a substituted or unsubstituted pyridin-3-yl group. Further, as a preferred example of the pyridyl group having a substituent(s), there may be mentioned 2-position or 4-position mono-substituted or 2,4-di-substituted pyridin-3-yl groups. Among them, as a more preferred example, there may be mentioned an unsubstituted pyridin-3-yl group or a 2-position substituted pyridin-3-yl group. Also, the substitution position of X on the benzene ring is not particularly limited, but there may be preferably mentioned x having a substitution position which is an ortho-position relative to the substitution position of a pyridazin-3(2H)-one portion on the benzene ring.

When the desired compound (I) of the present invention has asymmetric atoms, both of steric isomers based on the asymmetric atoms and a mixture thereof are included in the present invention.

Specific examples of the desired compound of the present invention are shown in the following Tables 1 to 5, but the desired compound of the present invention is not limited thereby.

TABLE 1

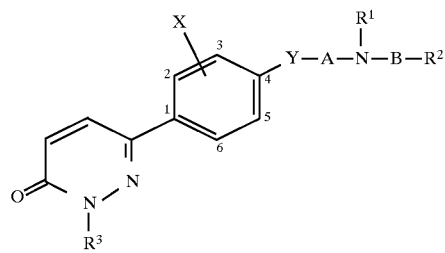

| X | —Y—A— | B | $R^1$ | $R^2$ | $R^3$ |
|---|---|---|---|---|---|
| H | —CH$_2$CH(CH$_3$)— | CO | H | n-propyl | H |
| H | —CH$_2$CH(CH$_3$)— | CO | H | ethyl | H |
| H | —CH$_2$CH(CH$_3$)— | CO | H | cyclopropyl | H |
| H | —CH$_2$CH(CH$_3$)— | CO | H | isobutyl | H |
| H | —CH$_2$CH(CH$_3$)— | CO | H | 4-pyridyl | H |
| H | —CH$_2$CH(CH$_3$)— | CO | n-propyl | 4-pyridyl | H |
| H | —CH$_2$CH(CH$_3$)— | CO | n-propyl | n-propyl | H |
| H | —CH$_2$CH(CH$_3$)— | CO | H | n-propylamino | H |
| H | —CH$_2$CH(CH$_3$)— | CO | H | n-propoxy | H |
| H | —CH$_2$CH(CH$_3$)— | CO | H | vinyloxy | H |
| H | —CH$_2$CH(CH$_3$)— | CO | n-propyl | phenoxy | H |
| H | —CH$_2$CH(CH$_3$)— | CO | n-propyl | isobutoxy | H |
| H | —CH$_2$CH(CH$_3$)— | CS | H | n-propylamino | H |
| H | —CH$_2$CH(CH$_3$)CH$_2$— | CO | H | n-propyl | H |
| H | —CH$_2$CH(CH$_3$)CH$_2$— | CO | H | vinyl | H |
| H | —CH$_2$CH(CH$_3$)CH$_2$— | CO | H | cyclopropyl | H |
| H | —CH$_2$CH(CH$_3$)CH$_2$— | CO | H | styryl | H |
| H | —CH$_2$CH(CH$_3$)CH$_2$— | CO | H | phenyl | H |

TABLE 1-continued

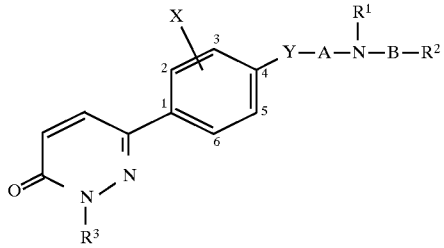

| X | —Y—A— | B | R¹ | R² | R³ |
|---|---|---|---|---|---|
| H | —CH₂CH(CH₃)CH₂— | CO | H | 3-thienyl | H |
| H | —CH₂CH(CH₃)CH₂— | CO | H | 3-pyridyl | H |
| H | —CH₂CH(CH₃)CH₂— | CO | H | n-propoxy | H |
| H | —CH₂CH(CH₃)CH₂CH₂— | CO | H | vinyloxy | H |
| H | —CH₂CH(CH₃)(CH₂)₄— | CO | H | vinyl | H |
| H | —CH₂CH(CH₃)(CH₂)₄— | CO | H. | n-propoxy | H |
| H | —CH₂CH(CH₃)CH₂— | CO | H | 2,2-dimethylvinyl | H |
| H | —CH₂CH(CH₃)CH₂— | CO | H | 2-propenylamino | H |
| H | —CH₂CH(CH₃)CH₂CH₂— | CS | H | n-propylamino | H |
| H | —CH₂CH(CH₃)— | CO | H | vinyl | H |
| H | —CH₂CH(CH₃)CH₂CH₂— | CO | n-propyl | n-propyl | H |
| H | —CH₂CH(CH₃)— | CO | n-propyl | n-propyl | H |
| H | —CH₂CH(CH₃)CH₂CH₂— | CO | H | vinyl | H |
| H | —CH₂CH(CH₃)(CH₂)₃— | CO | H | vinyl | H |
| H | —CH₂CH(CH₃)(CH₂)₅— | CO | H | vinyl | H |
| H | —CH₂CH(CH₃)(CH₂)₆— | CO | H | vinyl | H |
| H | —CH₂CH(CH₃)CH₂CH₂— | CO | H | 4-pyridyl | H |
| H | —CH₂CH(CH₃)CH₂CH₂— | CO | H | 3-pyridyl | H |
| H | —CH₂CH(CH₃)(CH₂)₃— | CO | H | 3-pyridyl | H |
| H | —CH₂CH(CH₃)(CH₂)₄— | CO | H | 3-pyridyl | H |
| H | —CH₂CH(CH₃)(CH₂)₅— | CO | H | 3-pyridyl | H |
| H | —CH₂CH(CH₃)(CH₂)₆— | CO | H | 3-pyridyl | H |
| H | —CH₂CH(CH₃)(CH₂)₃— | CO | H | methyl | H |
| H | —CH₂CH(CH₃)(CH₂)₃— | CO | H | ethyl | H |
| H | —CH₂CH(CH₃)(CH₂)₃— | CO | H | n-propyl | H |
| H | —CH₂CH(CH₃)(CH₂)₃— | CO | H | cyclopropyl | H |
| H | —CH₂CH(CH₃)(CH₂)₃— | CO | H | isobutyl | H |
| H | —CH₂CH(CH₃)CH₂CH₂— | CO | n-propyl | vinyl | H |
| H | —CH₂CH(CH₃)CH₂CH₂— | CO | n-propyl | 3-pyridyl | H |
| H | —CH₂CH(CH₃)(CH₂)₃— | CO | n-propyl | vinyl | H |
| H | —CH₂CH(CH₃)CH₂CH₂— | CO | H | 2-pyrazinyl | H |
| H | —CH₂CH(CH₃)CH₂CH₂— | CO | H | 6-chloro-3-pyridyl | H |
| H | —CH₂CH(CH₃)CH₂CH₂— | CO | H | 5-methoxy-3-pyridyl | H |
| H | —CH₂CH(CH₃)CH₂CH₂— | CO | H | 2-methyl-3-pyridyl | H |
| H | —CH₂CH(CH₃)CH₂CH₂— | CO | H | 3-quinolyl | H |
| H | —CH₂CH(CH₃)CH₂CH₂— | CO | H | 2-amino-3-pyridyl | H |
| H | —CH₂CH(CH₃)CH₂CH₂— | CO | H | 5-pyrimidinyl | H |
| H | —CH₂CH(CH₃)CH₂CH₂— | CO | H | 2-pyridyl | H |
| H | —CH₂CH(CH₃)(CH₂)₄— | CO | H | 1-methylvinyl | H |
| H | —CH₂CH(CH₃)(CH₂)₄— | CO | H | 1-propenyl | H |
| H | —CH₂CH(CH₃)(CH₂)₄— | CO | H | 1,3-butadienyl | H |
| H | —CH₂CH(CH₃)CH₂CH₂— | CO | H | 2-chloro-3-pyridyl | H |
| H | —CH₂CH(CH₃)CH₂CH₂— | CO | H | 2-methoxy-3-pyridyl | H |
| H | —CH₂CH(CH₃)CH₂CH₂— | CO | H | 2-methylthio-3-pyridyl | H |
| H | —CH₂CH(CH₃)CH₂CH₂— | CO | H | 2-hydroxy-3-pyridyl | H |
| H | —CH₂CH(CH₃)CH₂CH₂— | CO | H | 2-dimethylamino-3-pyridyl | H |
| H | —CH₂CH(CH₃)CH₂CH₂— | CO | H | 4-dimethylamino-3-pyridyl | H |
| H | —CH₂CH(CH₃)CH₂CH₂— | CO | H | 4-methoxy-3-pyridyl | H |
| H | —CH₂CH(CH₃)CH₂CH₂— | CO | H | 4-chloro-3-pyridyl | H |
| H | —CH₂CH(CH₃)CH₂CH₂— | CO | H | 3-pyridylmethyl | H |
| H | —CH₂CH(CH₃)CH₂CH₂— | CO | H | 2-phenoxy-3-pyridyl | H |
| H | —CH₂CH(CH₃)CH₂CH₂— | CO | H | 4-amino-3-pyridyl | H |
| H | —CH₂CH(CH₃)CH₂CH₂— | CO | H | 2,4-dimethyl-3-pyridyl | H |
| H | —CH₂CH(CH₃)CH₂CH₂— | CO | H | 4-methylthio-3-pyridyl | H |
| H | —CH₂CH(CH₃)CH₂CH₂— | CO | H | 2-methylamino-3-pyridyl | H |
| H | —CH₂CH(CH₃)CH₂CH₂— | CO | H | 4-methyl-3-pyridyl | H |
| H | —CH₂CH(CH₃)CH₂— | SO₂ | H | ethyl | H |

TABLE 1-continued

| X | —Y—A— | B | R¹ | R² | R³ |
|---|---|---|---|---|---|
| H | —CH₂CH(CH₃)CH₂— | SO₂ | H | n-propyl | H |
| H | —CH₂CH(CH₃)CH₂— | SO₂ | H | n-butyl | H |
| H | —CH₂CH(CH₃)CH₂— | SO₂ | H | vinyl | H |
| H | —CH₂CH(CH₃)CH₂— | SO₂ | n-propyl | vinyl | H |
| H | —CH₂CH(CH₃)CH₂CH₂— | SO₂ | H | ethyl | H |
| H | —CH₂CH(CH₃)CH₂CH₂— | SO₂ | H | n-propyl | H |
| H | —CH₂CH(CH₃)CH₂CH₂— | SO₂ | H | vinyl | H |
| H | —CH₂CH(CH₃)CH₂CH₂— | SO₂ | n-propyl | vinyl | H |
| H | —CH₂CH(CH₃)(CH₂)₄— | SO₂ | H | methyl | H |
| H | —CH₂CH(CH₃)(CH₂)₄— | SO₂ | H | n-propyl | H |
| H | —CH₂CH(CH₃)(CH₂)₄— | SO₂ | H | vinyl | H |
| H | —CH₂CH(CH₃)CH₂CH₂— | SO₂ | H | 3-pyridyl | H |
| H | —CH₂CH(CH₃)(CH₂)₃— | SO₂ | H | vinyl | H |
| H | —CH₂CH(CH₃)(CH₂)₃— | SO₂ | H | n-propyl | H |
| H | —CH₂CH(CH₃)(CH₂)₃— | SO₂ | n-propyl | n-propyl | H |
| H | —CH₂CH(CH₃)(CH₂)₅— | SO₂ | H | vinyl | H |
| H | —CH₂CH(CH₃)(CH₂)₆— | SO₂ | H | vinyl | H |
| H | —CH₂CH(CH₃)CH₂CH₂— | SO₂ | n-propyl | n-propyl | H |
| H | —CH₂CH(CH₃)(CH₂)₃— | SO₂ | n-propyl | vinyl | H |
| H | —CH₂CH(CH₃)(CH₂)₄— | SO₂ | n-propyl | vinyl | H |
| H | —CH₂CH(CH₃)— | SO₂ | n-propyl | n-butyl | 3-(1-imidazolyl)-propyl |
| H | —CH₂CH(CH₃)— | SO₂ | H | n-butyl | H |
| H | —CH₂CH(CH₃)— | SO₂ | n-propyl | n-butyl | H |
| H | —CH₂CH(CH₃)— | SO₂ | n-propyl | vinyl | H |
| H | —CH₂CH(CH₃)— | SO₂ | n-propyl | 2-methylthioethyl | H |
| H | —CH₂CH(CH₃)— | SO₂ | H | 2-methylthioethyl | H |
| H | —CH₂CH(CH₃)— | SO₂ | H | methyl | H |
| H | —CH₂CH(CH₃)— | SO₂ | H | n-propyl | H |
| H | —CH₂CH(CH₃)— | SO₂ | H | isopropyl | H |
| H | —CH₂CH(CH₃)— | SO₂ | H | isobutyl | H |
| H | —CH₂CH(CH₃)— | SO₂ | H | n-pentyl | H |
| H | —CH₂CH(CH₃)— | SO₂ | H | n-hexyl | H |
| H | —CH₂CH(CH₃)— | SO₂ | H | n-heptyl | H |
| H | —CH₂CH(CH₃)— | SO₂ | H | benzyl | H |
| H | —CH₂CH(CH₃)— | SO₂ | H | 4-fluorophenyl-methyl | H |
| H | —CH₂CH(CH₃)— | SO₂ | H | 3,4-dichloro-phenylmethyl | H |
| H | —CH₂CH(CH₃)— | SO₂ | H | 4-pyridylethyl | H |
| H | —CH₂CH(CH₃)— | SO₂ | H | 4-pyridylmethyl | H |
| H | —CH₂CH(CH₃)— | SO₂ | H | 3-phenylpropyl | H |
| H | —CH₂CH(CH₃)— | SO₂ | H | 3-thienylmethyl | H |
| H | —CH₂CH(CH₃)— | SO₂ | H | 3-thienyl | H |
| H | —CH₂CH(CH₃)— | SO₂ | H | vinyl | H |
| H | —CH₂CH(CH₃)— | SO₂ | methyl | n-butyl | H |
| H | —CH₂CH(CH₃)— | SO₂ | n-propyl | n-butyl | H |
| H | —CH₂CH(CH₃)— | SO₂ | benzyl | n-butyl | H |
| H | —CH₂CH(CH₃)— | SO₂ | 3-pyridyl-methyl | n-butyl | H |
| H | —CH₂CH(CH₃)— | SO₂ | 2-thienyl-methyl | n-butyl | H |
| H | —CH₂CH(CH₃)— | SO₂ | H | n-butyl | methyl |
| H | —CH₂CH(CH₃)— | SO₂ | H | n-butyl | benzyl |
| H | —CH₂CH(CH₃)— | SO₂ | n-propyl | 2-thienyl | H |
| H | —CH₂CH(CH₃)— | SO₂ | allyl | n-butyl | H |
| H | —CH₂CH(CH₃)— | SO₂ | H | n-butyl | benzyl |
| H | —CH₂CH(CH₃)— | SO₂ | H | n-butyl | 4-fluorophenyl-methyl |
| H | —CH₂CH(CH₃)— | SO₂ | H | n-butyl | 3,4-dichloro-phenylmethyl |
| H | —CH₂CH(CH₃)— | SO₂ | H | n-butyl | 3,4,5-trimeth-oxyphenylmethyl |
| H | —CH₂CH(CH₃)— | SO₂ | H | n-butyl | 2-thienylmethyl |

TABLE 1-continued

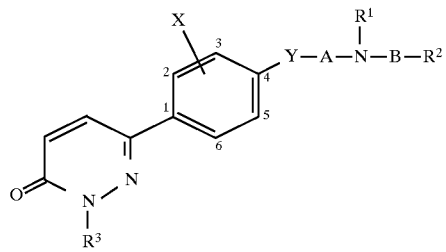

| X | —Y—A— | B | R¹ | R² | R³ |
|---|---|---|---|---|---|
| H | —CH₂CH(CH₃)— | SO₂ | H | n-butyl | 3-pyridylmethyl |
| H | —CH₂CH(CH₃)— | SO₂ | H | n-butyl | allyl |
| H | —CH₂CH(CH₃)— | SO₂ | H | n-butyl | 3-phenylpropyl |
| H | —CH₂CH(CH₃)— | SO₂ | H | n-butyl | 3-(4-morpholino)-propyl |
| H | —CH₂CH(CH₃)— | SO₂ | H | n-butyl | 2-dimethylamino-ethyl |
| H | —CH₂CH(CH₃)— | SO₂ | H | n-butyl | 2-(1-(4-tert-butoxy-carbonyl)piperazin-yl)ethyl |
| H | —CH₂CH(CH₃)— | SO₂ | H | n-butyl | 3-(1-imidazolyl)-propyl |
| H | —CH₂CH(CH₃)— | SO₂ | H | n-butyl | ethoxycarbonyl-methyl |
| H | —CH₂CH(CH₃)— | SO₂ | H | n-butyl | cyanomethyl |
| H | —CH₂CH(CH₃)— | SO₂ | H | n-butyl | dimethylcarba-moylmethyl |
| H | —CH₂CH(CH₃)— | SO₂ | H | n-butyl | 2-(1-piperazin-yl)ethyl |
| H | —CH₂CH(CH₃)— | SO₂ | H | n-butyl | hydroxycar-bonylmethyl |
| H | —CH₂CH(CH₃)— | SO₂ | H | n-butyl | 5-tetrazolyl-methyl |
| H | —CH₂CH(CH₃)— | SO₂ | methyl | n-butyl | hydroxycar-bonylmethyl |
| H | —CH₂CH(CH₃)— | SO₂ | 3-pyridyl-methyl | n-butyl | 3-pyridylmethyl |
| H | —CH₂CH(CH₃)— | SO₂ | H | n-butyl | H |
| H | —CH₂CH(CH₃)— | SO₂ | H | n-butyl | 2-dimethyl-aminoethyl |
| H | —CH₂CH(CH₃)— | SO₂ | methyl | n-butyl | ethoxycarbon-ylmethyl |
| H | —CH₂CH(CH₃)— | SO₂ | H | ethyl | H |
| H | —CH₂CH(CH₃)— | SO₂ | H | n-propyl | methyl |
| H | —(CH₂)₄— | CO | H | 3-pyridyl | H |
| H | —(CH₂)₃— | CO | H | 3-pyridyl | H |
| H | —(CH₂)₄— | CO | H | 2-methyl-3-pyridyl | H |
| H | —(CH₂)₄— | CO | H | 2-amino-3-pyridyl | H |
| H | —CH₂CH(CH₃)CH₂CH₂— | CO | H | 3-pyridyl | H |
| H | —CH₂CH(C₂H₅)CH₂CH₂— | CO | H | 3-pyridyl | H |
| H | —CH=CH—(CH₂)₂— | CO | H | 3-pyridyl | H |
| H | —O—(CH₂)₃— | CO | H | 3-pyridyl | H |
| H | —(CH₂)₅— | CO | H | 3-pyridyl | H |
| H | —(CH₂)₄— | CO | H | 4-pyridyl | H |
| H | —(CH₂)₄— | CO | H | 5-pyrid-azinyl | H |
| H | —(CH₂)₄— | CO | H | 3-pyrrolyl | H |
| H | —(CH₂)₄— | CO | ethyl | 3-pyridyl | H |
| H | —(CH₂)₃— | CO | H | vinyl | H |
| H | —(CH₂)₄— | CO | H | n-propyl | H |
| H | —(CH₂)₄— | CO | H | 4-chlorophenyl | H |
| H | —(CH₂)₃— | SO₂ | H | vinyl | H |
| H | —O—(CH₂)₃— | SO₂ | H | vinyl | H |
| H | —(CH₂)₄— | SO₂ | H | vinyl | H |
| H | —(CH₂)₅— | SO₂ | H | n-propyl | H |
| H | —(CH₂)₅— | SO₂ | H | vinyl | H |
| H | —(CH₂)₅— | SO₂ | ethyl | vinyl | H |
| H | —S—(CH₂)₃— | CO | H | 2-amino-3-pyridyl | H |
| H | —(CH₂)₅— | CO | H | 2-amino-3-pyridyl | H |
| H | —(CH₂)₄— | CO | H | vinyl | H |
| H | —(CH₂)₅— | CO | H | vinyl | H |
| H | —(CH₂)₆— | CO | H | 3-pyridyl | H |

TABLE 1-continued

| X | −Y−A− | B | R¹ | R² | R³ |
|---|---|---|---|---|---|
| H | −(CH₂)₆− | CO | H | 2-amino-3-pyridyl | H |
| H | −O−(CH₂)₄− | CO | H | 3-pyridyl | H |
| H | −O−(CH₂)₄− | CO | H | 2-amino-3-pyridyl | H |
| H | −O−(CH₂)₄− | SO₂ | H | vinyl | H |
| H | −O−(CH₂)₄− | CO | H | vinyl | H |
| H | −(CH₂)₄− | CO | H | 2-pirazinyl | H |
| H | −(CH₂)₄− | CO | H | 3-indolyl | H |
| H | −CH₂CH(CH₃)− | CO | H | 3-pyridyl | H |
| H | −CH₂CH(CH₃)− | CO | n-propyl | 3-pyridyl | H |
| 2-CH₃O | −(CH₂)₄− | CO | H | 3-pyridyl | H |
| 2-CH₃CONH | −(CH₂)₄− | CO | H | 3-pyridyl | H |
| 5-ClCH₂CH₂CH₂ | −(CH₂)₄− | CO | H | 3-pyridyl | H |
| 5-CH₃O₂CNHCH₂CH₂ | −(CH₂)₄− | CO | H | 3-pyridyl | H |
| 5-C₂H₅ | −(CH₂)₄− | CO | H | 3-pyridyl | H |
| 2-CH₃O | −(CH₂)₄− | SO₂ | H | vinyl | H |
| 2-CH₃CONH | −(CH₂)₄− | SO₂ | H | vinyl | H |
| 5-C₂H₅ | −(CH₂)₄− | SO₂ | H | vinyl | H |

TABLE 2

| X | −Y−A− | B | R¹ | R² | R³ |
|---|---|---|---|---|---|
| 2-Cl | −(CH₂)₄− | CO | H | 3-pyridyl | H |
| 2-CH₃O | −(CH₂)₄− | CO | H | 3-pyridyl | H |
| H | −(CH₂)₄− | CO | H | 3-pyridyl | H |
| 2-CH₃O | −(CH₂)₄− | SO₂ | H | vinyl | H |
| 2-Cl | −(CH₂)₄− | SO₂ | H | vinyl | H |
| H | −(CH₂)₄− | SO₂ | H | vinyl | H |
| H | −(CH₂)₄− | CO | H | 2-amino-3-pyridyl | H |
| H | −(CH₂)₅− | CO | H | 3-pyridyl | H |
| H | −(CH₂)₅− | CO | H | 2-amino-3-pyridyl | H |
| H | −(CH₂)₄− | CO | H | vinyl | H |
| H | −(CH₂)₆− | CO | H | 3-pyridyl | H |
| 2-CH₃S | −(CH₂)₄− | CO | H | 3-pyridyl | H |
| 2-CH₃CONH | −(CH₂)₄− | CO | H | 3-pyridyl | H |
| 2-CH₃OCH₂CH₂ | −(CH₂)₄− | CO | H | 3-pyridyl | H |
| 2-CH₃S | −(CH₂)₄− | SO₂ | H | vinyl | H |

TABLE 3

| X | −Y−A− | B | R¹ | R² | R³ |
|---|---|---|---|---|---|
| H | −(CH₂)₄− | SO₂ | H | vinyl | H |
| 5-Cl | −(CH₂)₄− | SO₂ | H | vinyl | H |
| 5-Cl | −(CH₂)₄− | CO | H | 3-pyridyl | H |
| H | −(CH₂)₄− | CO | H | 3-pyridyl | H |
| 4-CH₃O | −(CH₂)₄− | SO₂ | H | vinyl | H |
| 4-CH₃CONH | −(CH₂)₄− | CO | H | 3-pyridyl | H |
| 4-CH₃O | −(CH₂)₄− | CO | H | 3-pyridyl | H |

TABLE 4

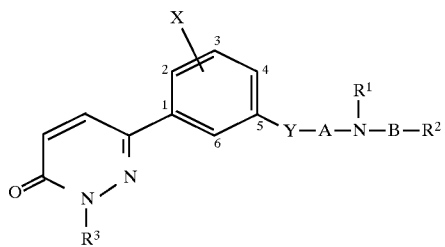

| X | —Y—A— | B | R¹ | R² | R³ |
|---|---|---|---|---|---|
| H | —CH₂CH(CH₃)— | CO | H | n-propyl | H |
| H | —CH₂CH(CH₃)— | CO | H | ethyl | H |
| H | —CH₂CH(CH₃)— | CO | H | cyclopropyl | H |
| H | —CH₂CH(CH₃)— | CO | H | isobutyl | H |
| H | —CH₂CH(CH₃)— | CO | H | 4-pyridyl | H |
| H | —CH₂CH(CH₃)— | CO | n-propyl | 4-pyridyl | H |
| H | —CH₂CH(CH₃)— | CO | n-propyl | n-propyl | H |
| H | —CH₂CH(CH₃)— | CO | H | n-propylamino | H |
| H | —CH₂CH(CH₃)— | CO | H | n-propoxy | H |
| H | —CH₂CH(CH₃)— | CO | H | vinyloxy | H |
| H | —CH₂CH(CH₃)— | CO | n-propyl | phenoxy | H |
| H | —CH₂CH(CH₃)— | CO | n-propyl | isobutoxy | H |
| H | —CH₂CH(CH₃)— | CS | H | n-propylamino | H |
| H | —CH₂CH(CH₃)CH₂— | CO | H | n-propyl | H |
| H | —CH₂CH(CH₃)CH₂— | CO | H | vinyl | H |
| H | —CH₂CH(CH₃)CH₂— | CO | H | cyclopropyl | H |
| H | —CH₂CH(CH₃)CH₂— | CO | H | styryl | H |
| H | —CH₂CH(CH₃)CH₂— | CO | H | phenyl | H |
| H | —CH₂CH(CH₃)CH₂— | CO | H | 3-thienyl | H |
| H | —CH₂CH(CH₃)CH₂— | CO | H | 3-pyridyl | H |
| H | —CH₂CH(CH₃)CH₂— | CO | H | n-propoxy | H |
| H | —CH₂CH(CH₃)CH₂CH₂— | CO | H | vinyloxy | H |
| H | —CH₂CH(CH₃)(CH₂)₄— | CO | H | vinyl | H |
| H | —CH₂CH(CH₃)(CH₂)₄— | CO | H | n-propoxy | H |
| H | —CH₂CH(CH₃)CH₂— | CO | H | 2,2-dimethylvinyl | H |
| H | —CH₂CH(CH₃)CH₂— | CO | H | 2-propenylamino | H |
| H | —CH₂CH(CH₃)CH₂CH₂— | CS | H | n-propylamino | H |
| H | —CH₂CH(CH₃)— | CO | H | vinyl | H |
| H | —CH₂CH(CH₃)CH₂CH₂— | CO | n-propyl | n-propyl | H |
| H | —CH₂CH(CH₃)— | CO | n-propyl | n-propyl | H |
| H | —CH₂CH(CH₃)CH₂CH₂— | CO | H | vinyl | H |
| H | —CH₂CH(CH₃)(CH₂)₃— | CO | H | vinyl | H |
| H | —CH₂CH(CH₃)(CH₂)₅— | CO | H | vinyl | H |
| H | —CH₂CH(CH₃)(CH₂)₆— | CO | H | vinyl | H |
| H | —CH₂CH(CH₃)CH₂CH₂— | CO | H | 4-pyridyl | H |
| H | —CH₂CH(CH₃)CH₂CH₂— | CO | H | 3-pyridyl | H |
| H | —CH₂CH(CH₃)(CH₂)₃— | CO | H | 3-pyridyl | H |
| H | —CH₂CH(CH₃)(CH₂)₄— | CO | H | 3-pyridyl | H |
| H | —CH₂CH(CH₃)(CH₂)₅— | CO | H | 3-pyridyl | H |
| H | —CH₂CH(CH₃)(CH₂)₆— | CO | H | 3-pyridyl | H |
| H | —CH₂CH(CH₃)(CH₂)₃— | CO | H | methyl | H |
| H | —CH₂CH(CH₃)(CH₂)₃— | CO | H | ethyl | H |
| H | —CH₂CH(CH₃)(CH₂)₃— | CO | H | n-propyl | H |
| H | —CH₂CH(CH₃)(CH₂)₃— | CO | H | cyclopropyl | H |
| H | —CH₂CH(CH₃)(CH₂)₃— | CO | H | isobutyl | H |
| H | —CH₂CH(CH₃)CH₂CH₂— | CO | n-propyl | vinyl | H |
| H | —CH₂CH(CH₃)CH₂CH₂— | CO | n-propyl | 3-pyridyl | H |
| H | —CH₂CH(CH₃)(CH₂)₃— | CO | n-propyl | vinyl | H |
| H | —CH₂CH(CH₃)CH₂CH₂— | CO | H | 2-pyrazinyl | H |
| H | —CH₂CH(CH₃)CH₂CH₂— | CO | H | 6-chloro-3-pyridyl | H |
| H | —CH₂CH(CH₃)CH₂CH₂— | CO | H | 5-methoxy-3-pyridyl | H |
| H | —CH₂CH(CH₃)CH₂CH₂— | CO | H | 2-methyl-3-pyridyl | H |
| H | —CH₂CH(CH₃)CH₂CH₂— | CO | H | 3-quinolyl | H |
| H | —CH₂CH(CH₃)CH₂CH₂— | CO | H | 2-amino-3-pyridyl | H |
| H | —CH₂CH(CH₃)CH₂CH₂— | CO | H | 5-pyrimidinyl | H |
| H | —CH₂CH(CH₃)CH₂CH₂— | CO | H | 2-pyridyl | H |
| H | —CH₂CH(CH₃)(CH₂)₄— | CO | H | 1-methylvinyl | H |
| H | —CH₂CH(CH₃)(CH₂)₄— | CO | H | 1-propenyl | H |
| H | —CH₂CH(CH₃)(CH₂)₄— | CO | H | 1,3-butadienyl | H |
| H | —CH₂CH(CH₃)CH₂CH₂— | CO | H | 2-chloro-3-pyridyl | H |
| H | —CH₂CH(CH₃)CH₂CH₂— | CO | H | 2-methoxy-3-pyridyl | H |
| H | —CH₂CH(CH₃)CH₂CH₂— | CO | H | 2-methylthio-3-pyridyl | H |
| H | —CH₂CH(CH₃)CH₂CH₂— | CO | H | 2-hydroxy-3-pyridyl | H |
| H | —CH₂CH(CH₃)CH₂CH₂— | CO | H | 2-dimethylamino-3-pyridyl | H |
| H | —CH₂CH(CH₃)CH₂CH₂— | CO | H | 4-dimethylamino- | H |

| | | | | | |
|---|---|---|---|---|---|
| H | —CH$_2$CH(CH$_3$)CH$_2$CH$_2$— | CO | H | 3-pyridyl 4-methoxy-3-pyridyl | H |
| H | —CH$_2$CH(CH$_3$)CH$_2$CH$_2$— | CO | H | 4-chloro-3-pyridyl | H |
| H | —CH$_2$CH(CH$_3$)CH$_2$CH$_2$— | CO | H | 3-pyridylmethyl | H |
| H | —CH$_2$CH(CH$_3$)CH$_2$CH$_2$— | CO | H | 2-phenoxy-3-pyridyl | H |
| H | —CH$_2$CH(CH$_3$)CH$_2$CH$_2$— | CO | H | 4-amino-3-pyridyl | H |
| H | —CH$_2$CH(CH$_3$)CH$_2$CH$_2$— | CO | H | 2,4-dimethyl-3-pyridyl | H |
| H | —CH$_2$CH(CH$_3$)CH$_2$CH$_2$— | CO | H | 4-methylthio-3-pyridyl | H |
| H | —CH$_2$CH(CH$_3$)CH$_2$CH$_2$— | CO | H | 2-methylamino-3-pyridyl | H |
| H | —CH$_2$CH(CH$_3$)CH$_2$CH$_2$— | CO | H | 4-methyl-3-pyridyl | H |
| H | —CH$_2$CH(CH$_3$)CH$_2$— | SO$_2$ | H | ethyl | H |
| H | —CH$_2$CH(CH$_3$)CH$_2$— | SO$_2$ | H | n-propyl | H |
| H | —CH$_2$CH(CH$_3$)CH$_2$— | SO$_2$ | H | n-butyl | H |
| H | —CH$_2$CH(CH$_3$)CH$_2$— | SO$_2$ | H | vinyl | H |
| H | —CH$_2$CH(CH$_3$)CH$_2$— | SO$_2$ | n-propyl | vinyl | H |
| H | —CH$_2$CH(CH$_3$)CH$_2$CH$_2$— | SO$_2$ | H | ethyl | H |
| H | —CH$_2$CH(CH$_3$)CH$_2$CH$_2$— | SO$_2$ | H | n-propyl | H |
| H | —CH$_2$CH(CH$_3$)CH$_2$CH$_2$— | SO$_2$ | H | vinyl | H |
| H | —CH$_2$CH(CH$_3$)CH$_2$CH$_2$— | SO$_2$ | n-propyl | vinyl | H |
| H | —CH$_2$CH(CH$_3$)(CH$_2$)$_4$— | SO$_2$ | H | methyl | H |
| H | —CH$_2$CH(CH$_3$)(CH$_2$)$_4$— | SO$_2$ | H | n-propyl | H |
| H | —CH$_2$CH(CH$_3$)(CH$_2$)$_4$— | SO$_2$ | H | vinyl | H |
| H | —CH$_2$CH(CH$_3$)CH$_2$CH$_2$— | SO$_2$ | H | 3-pyridyl | H |
| H | —CH$_2$CH(CH$_3$)(CH$_2$)$_3$— | SO$_2$ | H | vinyl | H |
| H | —CH$_2$CH(CH$_3$)(CH$_2$)$_3$— | SO$_2$ | H | n-propyl | H |
| H | —CH$_2$CH(CH$_3$)(CH$_2$)$_3$— | SO$_2$ | n-propyl | n-propyl | H |
| H | —CH$_2$CH(CH$_3$)(CH$_2$)$_5$— | SO$_2$ | H | vinyl | H |
| H | —CH$_2$CH(CH$_3$)(CH$_2$)$_6$— | SO$_2$ | H | vinyl | H |
| H | —CH$_2$CH(CH$_3$)CH$_2$CH$_2$— | SO$_2$ | n-propyl | n-propyl | H |
| H | —CH$_2$CH(CH$_3$)(CH$_2$)$_3$— | SO$_2$ | n-propyl | vinyl | H |
| H | —CH$_2$CH(CH$_3$)(CH$_2$)$_4$— | SO$_2$ | n-propyl | vinyl | H |
| H | —CH$_2$CH(CH$_3$)— | SO$_2$ | n-propyl | n-butyl | 3-(1-imidazolyl)-propyl |
| H | —CH$_2$CH(CH$_3$)— | SO$_2$ | H | n-butyl | H |
| H | —CH$_2$CH(CH$_3$)— | SO$_2$ | n-propyl | n-butyl | H |
| H | —CH$_2$CH(CH$_3$)— | SO$_2$ | n-propyl | vinyl | H |
| H | —CH$_2$CH(CH$_3$)— | SO$_2$ | n-propyl | 2-methylthioethyl | H |
| H | —CH$_2$CH(CH$_3$)— | SO$_2$ | H | 2-methylthioethyl | H |
| H | —CH$_2$CH(CH$_3$)— | SO$_2$ | H | methyl | H |
| H | —CH$_2$CH(CH$_3$)— | SO$_2$ | H | n-propyl | H |
| H | —CH$_2$CH(CH$_3$)— | SO$_2$ | H | isopropyl | H |
| H | —CH$_2$CH(CH$_3$)— | SO$_2$ | H | isobutyl | H |
| H | —CH$_2$CH(CH$_3$)— | SO$_2$ | H | n-pentyl | H |
| H | —CH$_2$CH(CH$_3$)— | SO$_2$ | H | n-hexyl | H |
| H | —CH$_2$CH(CH$_3$)— | SO$_2$ | H | n-heptyl | H |
| H | —CH$_2$CH(CH$_3$)— | SO$_2$ | H | benzyl | H |
| H | —CH$_2$CH(CH$_3$)— | SO$_2$ | H | 4-fluorophenylmethyl | H |
| H | —CH$_2$CH(CH$_3$)— | SO$_2$ | H | 3,4-dichlorophenylmethyl | H |
| H | —CH$_2$CH(CH$_3$)— | SO$_2$ | H | 4-pyridylmethyl | H |
| H | —CH$_2$CH(CH$_3$)— | SO$_2$ | H | 3-phenylpropyl | H |
| H | —CH$_2$CH(CH$_3$)— | SO$_2$ | H | 3-thienylmethyl | H |
| H | —CH$_2$CH(CH$_3$)— | SO$_2$ | H | 3-thienyl | H |
| H | —CH$_2$CH(CH$_3$)— | SO$_2$ | H | vinyl | H |
| H | —CH$_2$CH(CH$_3$)— | SO$_2$ | methyl | n-butyl | H |
| H | —CH$_2$CH(CH$_3$)— | SO$_2$ | n-propyl | n-butyl | H |
| H | —CH$_2$CH(CH$_3$)— | SO$_2$ | benzyl | n-butyl | H |
| H | —CH$_2$CH(CH$_3$)— | SO$_2$ | 3-pyridylmethyl | n-butyl | H |
| H | —CH$_2$CH(CH$_3$)— | SO$_2$ | 2-thienylmethyl | n-butyl | H |
| H | —CH$_2$CH(CH$_3$)— | SO$_2$ | H | n-butyl | methyl |
| H | —CH$_2$CH(CH$_3$)— | SO$_2$ | H | n-butyl | benzyl |
| H | —CH$_2$CH(CH$_3$)— | SO$_2$ | n-propyl | 2-thienyl | H |
| H | —CH$_2$CH(CH$_3$)— | SO$_2$ | allyl | n-butyl | H |
| H | —CH$_2$CH(CH$_3$)— | SO$_2$ | H | n-butyl | benzyl |
| H | —CH$_2$CH(CH$_3$)— | SO$_2$ | H | n-butyl | 4-fluorophenylmethyl |
| H | —CH$_2$CH(CH$_3$)— | SO$_2$ | H | n-butyl | 3,4-dichlorophenylmethyl |
| H | —CH$_2$CH(CH$_3$)— | SO$_2$ | H | n-butyl | 3,4,5-trimethoxyphenylmethyl |
| H | —CH$_2$CH(CH$_3$)— | SO$_2$ | H | n-butyl | 2-thienylmethyl |
| H | —CH$_2$CH(CH$_3$)— | SO$_2$ | H | n-butyl | 3-pyridylmethyl |
| H | —CH$_2$CH(CH$_3$)— | SO$_2$ | H | n-butyl | allyl |
| H | —CH$_2$CH(CH$_3$)— | SO$_2$ | H | n-butyl | 3-phenylpropyl |

| | | | | | |
|---|---|---|---|---|---|
| H | —CH$_2$CH(CH$_3$)— | SO$_2$ | H | n-butyl | 3-(4-morpholino)-propyl |
| H | —CH$_2$CH(CH$_3$)— | SO$_2$ | H | n-butyl | 2-dimethylaminoethyl |
| H | —CH$_2$CH(CH$_3$)— | SO$_2$ | H | n-butyl | 2-(1-(4-tert-butoxycarbonyl)piperazinyl)ethyl |
| H | —CH$_2$CH(CH$_3$)— | SO$_2$ | H | n-butyl | 3-(1-imidazolyl)-propyl |
| H | —CH$_2$CH(CH$_3$)— | SO$_2$ | H | n-butyl | ethoxycarbonylmethyl |
| H | —CH$_2$CH(CH$_3$)— | SO$_2$ | H | n-butyl | cyanomethyl |
| H | —CH$_2$CH(CH$_3$)— | SO$_2$ | H | n-butyl | dimethylcarbamoylmethyl |
| H | —CH$_2$CH(CH$_3$)— | SO$_2$ | H | n-butyl | 2-(1-piperazinyl)ethyl |
| H | —CH$_2$CH(CH$_3$)— | SO$_2$ | H | n-butyl | hydroxycarbonylmethyl |
| H | —CH$_2$CH(CH$_3$)— | SO$_2$ | H | n-butyl | 5-tetrazolylmethyl |
| H | —CH$_2$CH(CH$_3$)— | SO$_2$ | methyl | n-butyl | hydroxycarbonylmethyl |
| H | —CH$_2$CH(CH$_3$)— | SO$_2$ | 3-pyridylmethyl | n-butyl | 3-pyridylmethyl |
| H | —CH$_2$CH(CH$_3$)— | SO$_2$ | H | n-butyl | H |
| H | —CH$_2$CH(CH$_3$)— | SO$_2$ | H | n-butyl | 2-dimethylaminoethyl |
| H | —CH$_2$CH(CH$_3$)— | SO$_2$ | methyl | n-butyl | ethoxycarbonylmethyl |
| H | —CH$_2$CH(CH$_3$)— | SO$_2$ | H | ethyl | H |
| H | —CH$_2$CH(CH$_3$)— | SO$_2$ | H | n-propyl | methyl |
| H | —(CH$_2$)$_4$— | CO | H | 3-pyridyl | H |
| H | —(CH$_2$)$_3$— | CO | H | 3-pyridyl | H |
| H | —(CH$_2$)$_4$— | CO | H | 2-methyl-3-pyridyl | H |
| H | —(CH$_2$)$_4$— | CO | H | 2-amino-3-pyridyl | H |
| H | —CH$_2$CH(CH$_3$)CH$_2$CH$_2$— | CO | H | 3-pyridyl | H |
| H | —CH$_2$CH(C$_2$H$_5$)CH$_2$CH$_2$— | CO | H | 3-pyridyl | H |
| H | —CH=CH—(CH$_2$)$_2$— | CO | H | 3-pyridyl | H |
| H | —O—(CH$_2$)$_3$— | CO | H | 3-pyridyl | H |
| H | —(CH$_2$)$_5$— | CO | H | 3-pyridyl | H |
| H | —(CH$_2$)$_4$— | CO | H | 4-pyridyl | H |
| H | —(CH$_2$)$_4$— | CO | H | 5-pyridazinyl | H |
| H | —(CH$_2$)$_4$— | CO | H | 3-pyrrolyl | H |
| H | —(CH$_2$)$_4$— | CO | ethyl | 3-pyridyl | H |
| H | —(CH$_2$)$_3$— | CO | H | vinyl | H |
| H | —(CH$_2$)$_4$— | CO | H | n-propyl | H |
| H | —(CH$_2$)$_4$— | CO | H | 4-chlorophenyl | H |
| H | —(CH$_2$)$_3$— | SO$_2$ | H | vinyl | H |
| H | —O—(CH$_2$)$_3$— | SO$_2$ | H | vinyl | H |
| H | —(CH$_2$)$_4$— | SO$_2$ | H | vinyl | H |
| H | —(CH$_2$)$_5$— | SO$_2$ | H | n-propyl | H |
| H | —(CH$_2$)$_5$— | SO$_2$ | H | vinyl | H |
| H | —(CH$_2$)$_5$— | SO$_2$ | ethyl | vinyl | H |
| H | —S—(CH$_2$)$_3$— | CO | H | 2-amino-3-pyridyl | H |
| H | —(CH$_2$)$_5$— | CO | H | 2-amino-3-pyridyl | H |
| H | —(CH$_2$)$_4$— | CO | H | vinyl | H |
| H | —(CH$_2$)$_5$— | CO | H | vinyl | H |
| H | —(CH$_2$)$_6$— | CO | H | 3-pyridyl | H |
| H | —(CH$_2$)$_6$— | CO | H | 2-amino-3-pyridyl | H |
| H | —O—(CH$_2$)$_4$— | CO | H | 3-pyridyl | H |
| H | —O—(CH$_2$)$_4$— | CO | H | 2-amino-3-pyridyl | H |
| H | —O—(CH$_2$)$_4$— | SO$_2$ | H | vinyl | H |
| H | —O—(CH$_2$)$_4$— | CO | H | vinyl | H |
| H | —(CH$_2$)$_4$— | CO | H | 2-pyrazinyl | H |
| H | —(CH$_2$)$_4$— | CO | H | 3-indolyl | H |
| H | —CH$_2$CH(CH$_3$)— | CO | H | 3-pyridyl | H |
| H | —CH$_2$CH(CH$_3$)— | CO | n-propyl | 3-pyridyl | H |

TABLE 5

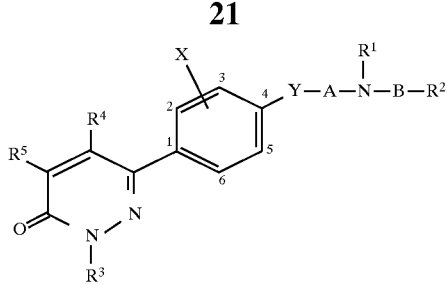

| X | —Y—A— | B | $R^1$ | $R^2$ | $R^3$ | $R^4$ | $R^5$ |
|---|---|---|---|---|---|---|---|
| H | —(CH$_2$)$_4$— | CO | H | 3-pyridyl | H | —CH$_3$ | H |
| H | —O—(CH$_2$)$_3$— | CO | H | 3-pyridyl | H | —CH$_3$ | H |
| H | —(CH$_2$)$_4$— | CO | H | 3-pyridyl | H | —CH$_3$ | —CH$_3$ |
| H | —(CH$_2$)$_4$— | CO | H | 3-pyridyl | H | H | —CH$_3$ |
| H | —(CH$_2$)$_2$— | CO | H | 3-pyridyl | H | —CH$_3$ | H |
| H | —(CH$_2$)$_4$— | CO | H | 3-pyridazinyl | H | H | H |
| H | —(CH$_2$)$_2$— | CO | H | 3-pyridyl | H | H | H |
| 5-CH$_3$ | —(CH$_2$)$_4$— | CO | H | 3-pyridyl | H | H | H |
| H | —(CH$_2$)$_4$— | CO | H | 3-methyl-5-isoxazolyl | H | H | H |

The desired compound (I) of the present invention can be used for medical uses either in a free form or in the form of a pharmaceutically acceptable salt thereof. As the pharmaceutically acceptable salt, there may be mentioned inorganic acid salts such as hydrochloride, sulfate, phosphate and hydrobromide, and organic acid salts such as acetate, succinate, fumarate, oxalate, maleate and methanesulfonate, particularly hydrochloride.

Further, the salt of the desired compound (I) may be in the form of a salt with a resin formed of, for example, a polyethylene resin having amino group, quaternary amino group or sulfonic acid group or a resin having carboxy group, for example, a polyacrylic acid resin. Also, the salt may be a complex with a metal such as iron and copper, or a ammonium chloride salt. Thus, it should be understood that the desired compound (I) and a salt thereof include all of intramolecular salts, adducts, complexes, solvates and hydrates thereof.

The desired compound (I) of the present invention can be administered either orally or parenterally, and it can be used as a medical preparation by mixing it with an excipient suitable for oral or parenteral administration. The medical preparation may be a solid preparation such as a tablet, a granule, a capsule and a powder, or a liquid preparation such as a solution, a suspension and an emulsion. Further, when the desired compound is administered parenterally, it can be used in the form of an injection.

The dose varies depending on age, weight and state of a patient and disease conditions of a patient, but, in general, the dose per day is preferably 1 to 300 mg/kg, particularly 3 to 100 mg/kg in the case of oral administration, and it is preferably 0.01 to 50 mg/kg, particularly 0.1 to 20 mg/kg in the case of parenteral administration.

According to the present invention, the desired compounds of the present invention can be prepared by the following processes.

Preparation process (A)

Among the desired compounds (I), a pyridazinone compound represented by the formula (I-a):

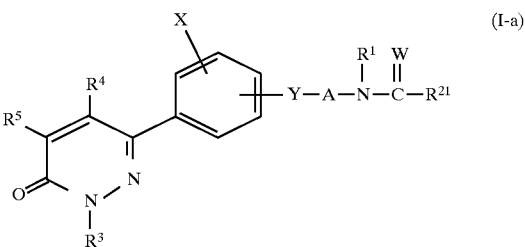

wherein W represents oxygen atom or sulfur atom; $R^{21}$ represents an alkyl group having 1 to 10 carbon atoms which may be substituted, a cycloalkyl group having 3 to 6 carbon atoms, a lower alkenyl group, a phenyl-substituted lower alkenyl group, a lower alkoxy group which may have a substituent(s), phenoxy group, a lower alkylamino group, a lower alkenylamino group, phenylamino group, a lower alkenyloxy group, a monocyclic or bicyclic heterocyclic aromatic group which has at least one of nitrogen atom, oxygen atom and sulfur atom as a hetero atom(s) and may have a substituent(s), or an aryl group which may have a substituent(s); and X, Y, A, $R^1$, $R^3$, $R^4$ and $R^5$ have the same meanings as defined above, or a pharmaceutically acceptable salt thereof can be prepared by, for example, reacting a pyridazinone compound represented by the formula (II):

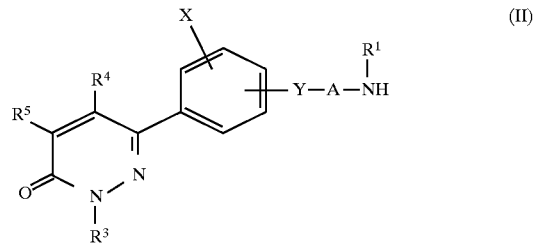

wherein X, Y, A, $R^1$, $R^3$, $R^4$ and $R^5$ have the same meanings as defined above, or a salt thereof with a compound represented by the formula (III):

wherein W and $R^{21}$ have the same meanings as defined above, a reactive derivative thereof or a salt thereof, and, if necessary, converting the resulting compound into a pharmaceutically acceptable salt thereof.

Preparation process (B)

Among the desired compounds (I), a pyridazinone compound represented by the formula (I-b):

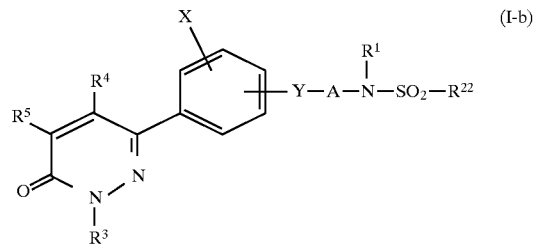

wherein $R^{22}$ represents an alkyl group having 1 to 10 carbon atoms which may be substituted, a cycloalkyl group having 3 to 6 carbon atoms, a lower alkenyl group, a phenyl-substituted lower alkenyl group or a monocyclic or bicyclic heterocyclic aromatic group which has at least one of nitrogen atom, oxygen atom and sulfur atom as a hetero atom(s) and may have a substituent(s); and X, Y, A, $R^1$, $R^3$, $R^4$ and $R^5$ have the same meanings as defined above, or a pharmaceutically acceptable salt thereof can be prepared by, for example, reacting a pyridazinone compound represented by the formula (II):

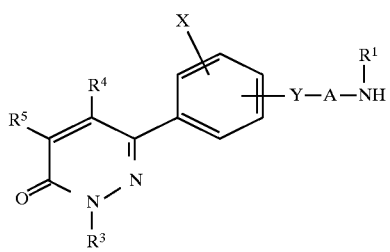

(II)

wherein X, Y, A, $R^1$, $R^3$, $R^4$ and $R^5$ have the same meanings as defined above, or a salt thereof with a compound represented by the formula (IV):

$R^{22}$—$SO_2Z$ (IV)

wherein Z represents a reactive residue; and $R^{22}$ has the same meaning as defined above, and, if necessary, converting the resulting compound into a pharmaceutically acceptable salt thereof.

Preparation process (C)

The desired compound (I) can be also prepared by, for example, oxidizing a compound represented by the formula (V):

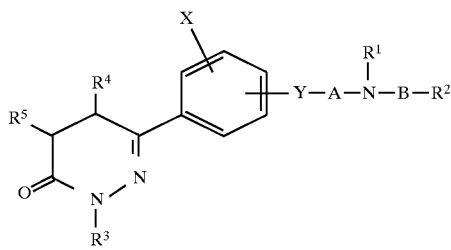

(V)

wherein X, Y, A, B, $R^1$, $R^2$, $R^3$, $R^4$ and $R^5$ have the same meanings as defined above, and, if necessary, converting the resulting compound into a pharmaceutically acceptable salt thereof.

In Preparation process (A) described above, when the compound (I-a) is prepared by using the compound (III) or a salt thereof, the reaction can be carried out in the presence or absence of a condensing agent, if necessary, in the presence of an acid acceptor in a suitable solvent.

As the condensing agent, there may be used a conventional condensing agent such as 1,3-dicyclohexylcarbodiimide, carbonyldiimidazole, 1-ethyl-3-(3'-dimethylaminopropyl)carbodiimide and diethylphosphoric cyanide. As the salt of the compound (III), there may be used a conventionally used salt such as an alkali metal salt, an alkaline earth metal salt and an organic amine salt. It is preferred that in the reaction with the compound (II), the above salt is previously converted into a free compound and then provided for the reaction.

In Preparation process (A), when the compound (I-a) is prepared by using the reactive derivative of the compound (III), the reaction can be optionally carried out in a suitable solvent in the presence of absence of an acid acceptor. As the reactive derivative, there may be used any reactive derivative conventionally used for condensation, for example, acid halide, mixed acid anhydride and active ester. As the salt of the reactive derivative, there may be used, for example, a salt of an inorganic acid such as hydrochloric acid, hydrobromic acid and sulfuric acid.

In Preparation process (B), when the compound (I-b) is prepared by using the compound (IV), the reaction can be carried out in the presence of an acid acceptor in a suitable solvent.

Also, the compound (I-b) can be prepared by once converting the compound (II) into an aminosilyl derivative in the reaction system by using an agent for introducing a silyl group such as trimethylchlorosilane, triethylchlorosilane and tert-butyldimethylchlorosilane and then using the compound (IV).

As the reactive residue of the compound (IV), there may be mentioned, a group which eliminates nucleophilically, for example, a halogen atom, an alkoxy group, a lower alkylsulfonyloxy group, benzenesulfonyloxy group, a lower alkyl group-substituted benzenesulfonyloxy group and trifluoromethanesulfonyloxy group.

In Preparation process (A) and Preparation process (B) described above, as the salt of the compound (II), there may be used, for example, a salt of an inorganic acid such as hydrochloric acid, hydrobromic acid, sulfuric acid, and phosphoric acid or a salt of an organic acid such as succinic acid, fumaric acid, and maleic acid.

As the acid acceptor to be used in Preparation process (A) and Preparation process (B) described above, there may be mentioned an alkali metal carbonate such as potassium carbonate and sodium carbonate, an alkali metal hydrogen carbonate such as potassium hydrogen carbonate and sodium hydrogen carbonate, an alkali metal hydroxide such as sodium hydroxide and potassium hydroxide, a tri-lower alkylamine such as triethylamine, tributylamine and diisopropylethylamine, a tertiary amine such as 1,4-diazabicyclo[2.2.2]octane, 1,5-diazabicyclo[4.3.0]non-5-ene and 1,8-diazabicyclo(5.4.0]undec-7-ene, and an aromatic amine such as pyridine, lutidine, collidine and dimethylaniline.

The solvent to be used in Preparation process (A) and Preparation process (B) described above may be any inert solvent which does not exert bad influence on both of the reactions of Preparation processes (A) and (B), and may include, for example, a halogenated solvent such as chloroform, dichloromethane and dichloroethane; an aromatic hydrocarbon such as toluene and xylene; an ether type solvent such as tetrahydrofuran, dioxane, diethyl ether and 1,2-dimethoxyethane; a ketone type solvent such as acetone and methyl ethyl ketone; an ester type solvent such as ethyl acetate; acetonitrile; pyridine; 2,6-lutidine; dimethylformamide; dimethylsulfoxide; 1,3-dimethyl-2-imidazolidinone; a mixed solvent of these solvents; and a combination of any of these solvents and water.

Preparation processes (A) and (B) can be carried out under cooling to under heating, for example, preferably −30° C. to 150° C., particularly −10° C. to room temperature.

The oxidation in Preparation process (C) can be carried out according to the conventional method, and it can be suitably carried out by, for example, treating the compound (V) with sodium 3-nitrobenzenesulfonate in a suitable solvent under basic conditions; subjecting it to redox reaction by using dimethylsulfoxide in hydrogen bromide-acetic acid under acidic conditions; or halogenating it with bromine, chlorine or the like and immediately subjecting the halogenated compound to dehydrohalogenation.

As the solvent, there may be used suitably water, acetic acid, propionic acid, trifluoroacetic acid, methanesulfonic acid or a hydrogen bromide-acetic acid solution.

In the reactions of the present invention, when a compound having asymmetric atoms is used as the starting compound (II) or (V), a corresponding desired compound (I), (I-a) or (I-b) can be obtained, respectively, without racemization of the asymmetric atoms.

The starting compound (II) of the present invention can be prepared by reacting a compound represented by the formula (VI):

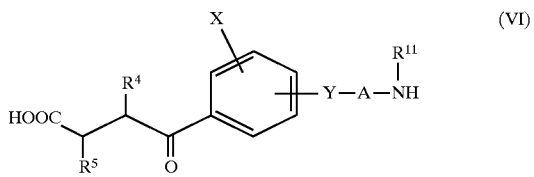

wherein $R^{11}$ represents hydrogen atom, a lower alkyl group which may be substituted or a lower alkenyl group; and X, Y, A, $R^4$ and $R^5$ have the same meanings as defined above, with hydrazine and when $R^{11}$ represents hydrogen atom, if desired, alkylating the amino group by, for example, a method of subjecting the amino group and a corresponding aldehyde compound to reductive alkylation in the presence of a suitable reducing agent such as sodium borohydride ($NaBH_4$) and sodium borotriacetoxy hydride [$NaB(OCOCH_3)_3H$], followed by oxidation.

In the above reaction, the reaction of the compound (VI) and hydrazine can be suitably carried out in a suitable solvent or in the absence of a solvent.

The solvent may be any inert solvent which does not exert bad influence on the reaction, and may include, for example, a lower alcohol such as methanol and ethanol, a lower aliphatic acid such as acetic acid and propionic acid, an aromatic hydrocarbon such as toluene and xylene, an ether such as tetrahydrofuran and dioxane, water, and the mixture of the above solvent and water. The reaction can be suitably carried out at a wide range of temperature from room temperature to the boiling point of a reaction mixture, for example, preferably 10° C. to 200° C., particularly 20° C. to 150° C.

The oxidation can be carried out in the same manner as in the oxidation of Preparation process (C) described above.

The starting compound (VI) can be prepared by, for example, a method in which, if necessary, after the amino group of a compound represented by the formula (VII):

wherein X, Y, A and $R^{11}$ have the same meanings as defined above is protected, said compound is reacted with a compound represented by the formula (VIII):

wherein $R^6$ represents an ester residue; and Z has the same meaning as defined above, or a compound represented by the formula (IX):

wherein $R^{41}$ represents a lower alkyl group; and $R^{51}$ represents a lower alkyl group, and then the ester residue and/or the protective group is/are removed.

Also, the starting compound (VI) can be prepared by, for example, a method in which after the amino group of the compound represented by the formula (VII):

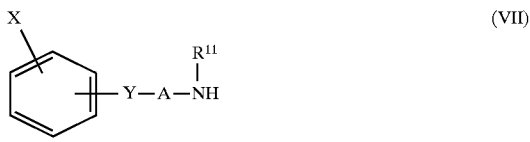

wherein X, Y, A and $R^{11}$ have the same meanings as defined above is protected, said compound is reacted with a compound represented by the formula (X):

wherein V represents a halogen atom; and Z and $R^{41}$ have the same meanings as defined above, to produce a compound represented by the formula (XI):

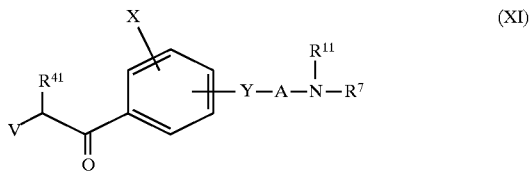

wherein $R^7$ represents a protective group for an amino group; and X, Y, A, V, $R^{11}$ and $R^{41}$ have the same meanings as defined above, the produced compound is reacted with a compound represented by the formula (XII):

wherein $R^6$ has the same meaning as defined above to produce a compound represented by the formula (XIII):

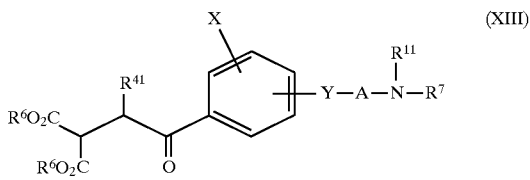

wherein X, Y, A, $R^6$, $R^7$, $R^{11}$ and $R^{41}$ have the same meanings as defined above, and then the produced compound is hydrolyzed and/or the protective group is removed.

Further, the starting compound (VI) can be prepared by, for example, a method in which after the amino group of the compound represented by the formula (VII):

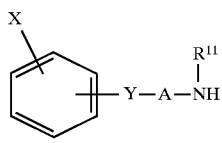

(VII)

wherein X, Y, A and $R^{11}$ have the same meanings as defined above
is protected, said compound is reacted with a compound represented by the formula (XIV):

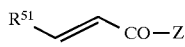

(XIV)

wherein Z and $R^{51}$ have the same meanings as defined above
to produce a compound represented by the formula (XV):

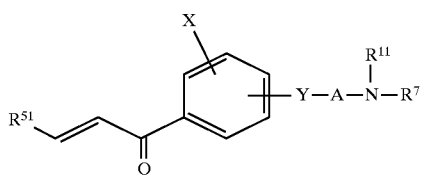

(XV)

wherein X, Y, A, $R^7$, $R^{11}$ and $R^{51}$ have the same meanings as defined above,
the produced compound is reacted with acetocyanohydrin or the like to produce a compound represented by the formula (XVI):

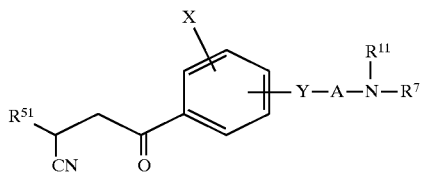

(XVI)

wherein X, Y, A, $R^7$, $R^{11}$ and $R^{51}$ have the same meanings as defined above,
and the produced compound is hydrolyzed and/or the protective group is removed.

As the protective group for the amino group, there may be mentioned a conventionally used protective group which can be a protective group for an amino group, for example, an acyl group such as acetyl group and phthaloyl group.

As the ester residue, there may be mentioned, for example, a lower alkyl group.

In the present specification, as the lower alkyl group, there may be mentioned, for example, an alkyl group having 1 to 6 carbon atoms such as methyl group, ethyl group, n-propyl group, isopropyl group, n-butyl group, sec-butyl group, tert-butyl group, n-pentyl group, isopentyl group, neopentyl group and n-hexyl group, preferably 1 to 4 carbon atoms, particularly 1 to 3 carbon atoms. As the lower alkoxy group, there may be mentioned, for example, an alkoxy group having 1 to 6 carbon atoms such as methoxy group, ethoxy group, propoxy group, isopropoxy group, butoxy group, pentyloxy group and isopentyloxy group, particularly 1 to 4 carbon atoms. As the lower alkenyl group, there may be mentioned, for example, alkenyl groups having 2 to 7 carbon atoms such as vinyl group, 1-propenyl group, allyl group, 1-methylallyl group, 1-, 2- or 3-butenyl group, 1-, 2-, 3- or 4-pentenyl group and 1-, 2-, 3-, 4- or 5-hexenyl group, particularly 2 to 5 carbon atoms.

In the present specification, the substituted amino group includes all of a mono-lower alkylamino group, a di-lower alkylamino group, an acylamino group, a N-lower alkyl-N-lower alkoxycarbonylamino group, a N-lower alkyl-N-carbamoylamino group, a N-lower alkyl-N-thiocarbamoylamino group (the nitrogen atom of said carbamoyl group or thiocarbamoyl group may be further substituted by 1 or 2 lower alkyl groups) and a lower alkylcarbamoyl group, and further includes an amino group in which the ends of two substituents on the nitrogen atom are bonded to form a cyclic structure, such as pyrrolidino group, piperidino group, perhydroazepin-1-yl group, morpholino group, thiomorpholino group and piperazino group (the nitrogen atom at 4-position of said piperazino group may be further substituted by a lower alkyl group, a lower alkenyl group, an acyl group, an aryl group or the like).

As the acyl group, there may be mentioned, for example, formyl group; a lower alkylcarbonyl group having 2 to 7 carbon atoms such as acetyl group, propionyl group, butyryl group, isobutyryl group, pivaloyl group and hexanoyl group, preferably 2 to 4 carbon atoms; and a lower alkoxycarbonyl group having 2 to 7 carbon atoms such as methoxycarbonyl group, ethoxycarbonyl group, propoxycarbonyl group, butoxycarbonyl group, tert-butoxycarbonyl group, pentyloxycarbonyl group and hexyloxycarbonyl group, preferably 2 to 4 carbon atoms.

The lower alkyl group, the lower alkoxy group and the lower alkenyl group may be straight or branched.

As the halogen atom, there may be mentioned chlorine, bromine, fluorine and iodine.

EXAMPLES

The present invention is described in detail by referring to Test examples and Examples, but the present invention is not limited by these examples. In Examples 1 to 29, Examples 65 and 66, Examples 77 to 86 and Example 88, starting compounds are described, and in Examples 30 to 64, Examples 67 to 76, Example 87, and Examples 89 to 103, desired compounds are described.

Test Example 1

Antinephritic Action

Rabbits were immunized several times with an adjuvant and a renal glomerular basement membrane fraction obtained from WKY rats, and then whole blood was collected from the rabbits to obtain a nephrotoxic serum (NTS). This NTS was diluted by 50 times with physiological saline, and to male WKY rats of 8 weeks old, 2.5 ml of the diluted NTS per 1 kg of body weight was injected intravenously to induce nephritis. To a normal group, the same amount of physiological saline was administered intravenously.

One experimental group consisted of 6 rats. Each compound to be tested was suspended in purified water by using a small amount of Tween 80 (trade name, produced by Nacalai Tesque Co.), and a dose of 30 mg/kg/10 ml was orally administered twice a day for continuous 8 days. To a normal group and a control group, the same amount of purified water was administered orally. On the seventh day, the rats were placed in a metabolic cage, and urine was collected for 24 hours. By measuring the concentrations of protein in urine by the sulfosalicylic acid method, the amounts of excreted protein (mg/day) were determined, and protein excretion-inhibiting rates were calculated by the following equation.

$$\text{Protein excretion inhibiting rate (\%)} = 100 - \frac{\begin{array}{c}\text{Amount of excreted}\\\text{protein of group}\\\text{to which a compound}\\\text{is administered}\end{array} - \begin{array}{c}\text{Amount of excreted}\\\text{protein of normal}\\\text{group}\end{array}}{\begin{array}{c}\text{Amount of excreted}\\\text{protein of control}\\\text{group}\end{array} - \begin{array}{c}\text{Amount of excreted}\\\text{protein of normal}\\\text{group}\end{array}} \times 100$$

The results are shown in Table 6. As can be clearly seen from Table 6, protein excretion of the groups to which the desired compound of the present invention was administered was inhibited at a high inhibition rate of about 65 to 90%.

TABLE 6

| Compound to be tested | Inhibition rate (%) |
| --- | --- |
| Example 30 | 82.5 |
| Example 32 | 64.3 |
| Example 33 | 85.7 |
| Example 36 | 89.0 |
| Example 52-(4) | 74.6 |
| Example 69 | 82.2 |
| Example 70 | 74.1 |

Test Example 2

Side Effect to Circulatory System

One experimental group consisted of 4 rats. Each compound to be tested was suspended in purified water by using a small amount of Tween 80 (trade name, produced by Nacalai Tesque Co.), and a dose of 30 mg/kg/10 ml was administered orally to normal awakened rats. Systolic blood pressures and heart rates before administration and 2 hours after administration were examined. The systolic blood pressures and the heart rates were measured by the tail-cuff method (KN-210, trade name, produced by Natsume Seisakusho) under conditions of pretreatment at 40° C. for 15 minutes.

According to the following equations, the respective changing rates were calculated.

$$\text{Systolic blood pressure changing rate (\%)} = \frac{\begin{array}{c}\text{Systolic blood}\\\text{pressure 2 hours}\\\text{after a compound}\\\text{is administered}\end{array} - \begin{array}{c}\text{Systolic blood}\\\text{pressure before}\\\text{a compound is}\\\text{administered}\end{array}}{\text{Systolic blood pressure before a compound is administered}} \times 100$$

$$\text{Heart rate changing rate (\%)} = \frac{\begin{array}{c}\text{Heart rate 2 hours}\\\text{after a compound}\\\text{is administered}\end{array} - \begin{array}{c}\text{Heart rate before}\\\text{a compound is}\\\text{administered}\end{array}}{\text{Heart rate before a compound is administered}} \times 100$$

The results are shown in Table 7.

TABLE 7

| Compound to be tested | Systolic blood pressure-changing rate (Δ%) | Heart rate-changing rate (Δ%) |
| --- | --- | --- |
| Example 30 | -2 | 3 |
| Example 31 | 0 | 7 |
| Example 32 | -2 | 5 |
| Example 33 | 1 | 2 |
| Example 36 | 0 | 1 |
| Known compound*) | -7 | 18 |

*)Known compound: 5-methyl-6-(4-[2-(pyridin-3-ylcarbonylamino)ethyl]phenyl)-4,5-dihydropyridazin-3(2H)-one (a compound described in Japanese Provisional Patent Publication No. 124279/1978)

As can be clearly seen from Table 7, it can be understood that the desired compounds of the present invention exert less influence on a heart rate and blood pressure and have less side effect to a circulatory system.

Test Example 3

Side Effect to Circulatory System

Twelve male and female mongrel dogs (6 dogs per one compound to be tested) were anesthetized by intravenous administration of 30 mg/kg of pentobarbital sodium. Thereafter, the depth of anesthesia was maintained by continuous injection of 5 mg/kg/hr of pentobarbital sodium, and artificial respiration was carried out by inserting tubes into tracheae. From left and right femoral veins, cannulas for injecting an anesthetic solution and cannulas for administering each compound to be tested were inserted, respectively. From right femoral arteries, cannulas for measuring blood pressure were inserted, and the end portions of the cannulas were kept in abdominal arteries. From left common carotid arteries, cannulas for measuring left ventricle pressure were inserted, and the end portions of the cannulas were kept in left ventricles. The compound to be tested was dissolved in a 25% hydroxy-β-cyclodextrin solution and administered intravenously. The amount of the solution to be administered was made 0.15 ml/kg. The compound to be tested was administered in a dose of 300 µg/kg, and blood pressures, heart rates and left ventriclular pressure before administration and until 1 hour after administration were examined. As the index of cardiac contractility, the maximum raising rate of left ventriclular pressure (LVdp/dtmax) was used. The blood pressures were measured from the artery cannulas by using a pressure amplifier (AP-621G, trade name, manufactured by Nihon Kodensha) via a pressure transducer (TP-400T, trade name, manufactured by Nihon Kodensha), and mean blood pressures were determined via a resistor-capacity circuit (AD-601G, trade name, manufactured by Nihon Kodensha, time constant: 3 seconds). With respect to the left ventriclular pressure, the left ventricles were measured in the same manner as in the case of the blood pressures by using the pressure amplifier via a micro-tip catherter pressure transducer (SPC-350, trade name, manufactured by Millar Instruments), and the values of LVdp/dtmax (the maximum raising rates of LVP) were determined by a differential amplifier (EQ-601G, trade name, manufactured by Nihon Kodensha). Further, the heart rates were measured by a heart rate meter (AC-601G, trade name, manufactured by Nihon Kodensha) with left ventricle pressure pulse waves as a trigger.

According to the following equations, the respective changing rates of the blood pressures, the heart rates and LVdp/dtmax were calculated.

$$\text{Blood pressure changing rate (\%)} = \frac{\text{Blood pressure} - \text{Blood pressure before a compound is administered}}{\text{Blood pressure before a compound is administered}} \times 100$$

$$\text{Heart rate changing rate (\%)} = \frac{\text{Heart rate} - \text{Heart rate before a compound is administered}}{\text{Heart rate before a compound is administered}} \times 100$$

$$LVdp/dt\text{max changing rate (\%)} = \frac{LVdp/dt\text{max} - LVdp/dt\text{max before a compound is administered}}{LVdp/dt\text{max before a compound is administered}} \times 100$$

The values when the respective changing rates were maximum between administration of the compounds to be tested and 1 hour after administration are shown in Table 8.

TABLE 8

| Compound to be tested | Blood pressure maximum changing rate (Δ%) | Heart rate maximum changing rate (Δ%) | LVdp/dtmax maximum changing rate (Δ%) |
|---|---|---|---|
| Example 69 | 0 | −0.6 | 3.3 |
| Known compound* | −11.3 | 20.1 | 44.3 |

*)Known compound: same as mentioned above.

As can be clearly seen from Table 8, it can be understood that the desired compounds of the present invention exert less influence on a heart rate, blood pressure and a left ventricle pressure-raising rate LVdp/dtmax (i.e., systolic power of a left ventricle) and have less side effect to a circulatory system.

Example 1

45.9 g of oxalyl chloride and 5 drops of dimethylformamide were added to a dichloroethane solution (500 ml) containing 45.5 g of methyl hydrogen succinate, and the mixture was stirred at room temperature for 3 hours. Under ice cooling, a dichloroethane solution (60 ml) containing 31.3 g of [4-(acetylamino)butyl]benzene, and 91.9 g of anhydrous aluminum chloride were added thereto, and the mixture was stirred for 1 hour. The reaction mixture was poured into ice water, and the organic layer was collected by separation. After the organic layer was washed with water and dried, the solvent was removed. The resulting crude crystal was recrystallized from ethyl acetate to obtain 42.3 g of 4-[4-(acetylamino)butyl]-1-(3-methoxycarbonylpropionly)benzene.

m.p.: 94° to 95° C.

Examples 2 to 5

By treating corresponding starting compounds in the same manner as in Example 1, compounds shown in Table 9 were obtained.

TABLE 9

| Example No. | Formula | Physical properties |
|---|---|---|
| 2 | CH$_3$O$_2$C—(CH$_2$)$_2$—CO—C$_6$H$_4$—(CH$_2$)$_3$NHCOCH$_3$ | m.p. 81 to 82° C. |
| 3 | CH$_3$O$_2$C—(CH$_2$)$_2$—CO—C$_6$H$_4$—(CH$_2$)$_5$NHCOCH$_3$ | m.p. 98 to 99° C. |
| 4 | CH$_3$O$_2$C—(CH$_2$)$_2$—CO—C$_6$H$_3$(Cl)—(CH$_2$)$_4$NHCOCH$_3$ | IR (neat)cm$^{-1}$: 3150 to 3450, 1740, 1700, 1650; MS (ESI) m/z: 340 (MH$^+$) |
| 5 | (CH$_2$)$_4$NHCOCH$_3$ and CO$_2$CH$_3$ substituents on Cl-substituted benzene with CO group | IR (neat) cm$^{-1}$: 3150 to 3700, 1740, 1700, 1650; MS (ESI) m/z: 340 (MH$^+$) |

Example 6

In 480 ml of 10M hydrochloric acid was suspended 43.0 g of 4-[4-(acetylamino)butyl]-1-(3-methoxycarbonylpropionyl)benzene, and the mixture was refluxed under heating overnight. 10M hydrochloric acid was removed, 350 ml of acetic acid and 20.7 g of hydrazine monohydrate were added to the resulting crude crystal (36.5 g), and the mixture was refluxed under heating for 3 hours. The mixture was concentrated until the amount of acetic acid became a half amount, 400 ml of ethyl ether was added to the concentrate, and precipitated crystal was collected by filtration. The crystal was dissolved in 200 ml of water, and the solution was neutralized with aqueous ammonia. Precipitated crystal was collected by filtration, dried and then recrystallized from methanol to obtain 30.1 g of 6-[4-(4-aminobutyl)phenyl]-4,5-dihydropyridazin-3(2H)-one.

m.p.: 167° to 168° C.

Examples 7 to 10

By treating corresponding starting compounds in the same manner as in Example 6, compounds shown in Table 10 were obtained.

TABLE 10

| Example No. | $X$—⟨phenyl⟩—Y—A—NH$_2$ | Physical properties |
|---|---|---|
| 7 | ⟨4-methylphenyl⟩—CH$_2$CH$_2$—NH$_2$ | m.p. 193 to 194° C. |
| 8 | ⟨4-methylphenyl⟩—(CH$_2$)$_5$NH$_2$ | m.p. 168 to 169° C. |
| 9 | ⟨3-Cl, 4-methylphenyl⟩—(CH$_2$)$_3$—NH$_2$ | m.p. 109 to 110° C. |
| 10 | ⟨3-Cl, 4-methylphenyl⟩—(CH$_2$)$_4$—NH$_2$ | m.p. 72 to 74° C. |

Example 11

Under ice cooling, 24.86 g of anhydrous aluminum chloride was added to a dichloroethane suspension (250 ml) containing of [2-methyl-4-phthalimidobutyl]benzene and 9.29 g of succinic anhydride, and the mixture was stirred temperature for 2 hours. The reaction mixture was poured into ice water, and the organic layer was collected by separation. After the organic layer was washed with water and dried, the solvent was removed. The resulting crude crystal was recrystallized from ethyl acetate-hexane to obtain 16.11 g of 4-(2-methyl-4-phthalimidobutyl)-1-(3-hydroxycarbonylpropionyl)benzene.

m.p.: 142° to 143° C.

Examples 12 to 14

By treating corresponding starting compounds in the same manner as in Example 11, compounds shown in Table 11 were obtained.

TABLE 11

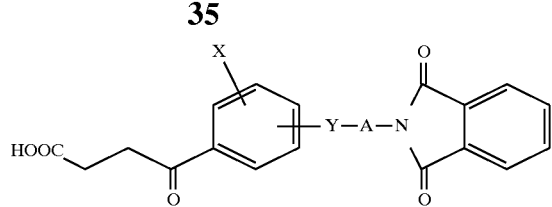

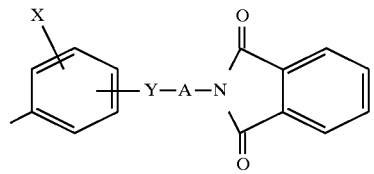

| Example No. | | Physical properties |
|---|---|---|
| 12 | 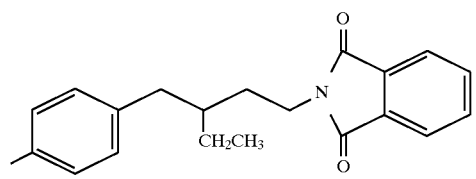 | m.p. 105 to 107° C. |
| 13 | 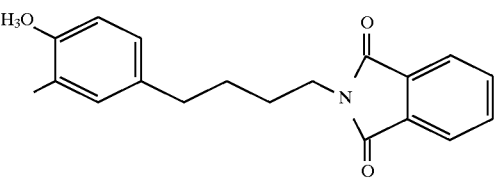 | m.p. 141 to 142° C. |
| 14 | 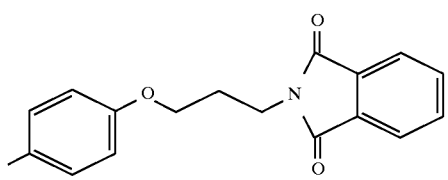 | m.p. 172 to 173° C. |

Example 15

9.61 g of hydrazine monohydrate was added to an ethanol solution (500 ml) containing 15.06 g of 4-(2-methyl-4-phthalimidobutyl)-1-(3-hydroxycarbonylpropionyl)benzene, and the mixture was refluxed under heating for 2.5 hours. After cooling, precipitated crystal was collected by filtration and recrystallized from ethyl acetate to obtain 8.14 g of 6-[4-(4-amino-2-methylbutyl)phenyl]-4,5-dihydropyridazin-3(2H)-one.

m.p.: 112° to 114° C.

Examples 16 to 18

By treating corresponding starting compounds in the same manner as in Example 15, compounds shown in Table 12 were obtained.

TABLE 12

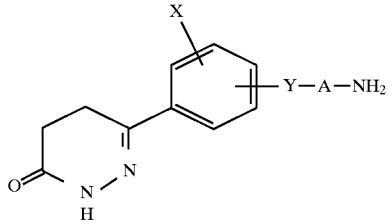

| Example No. | 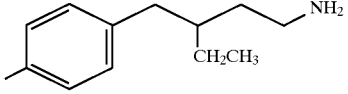 | Physical properties |
|---|---|---|
| 16 | 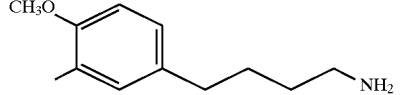 | m.p. 128 to 129 °C. |
| 17 | 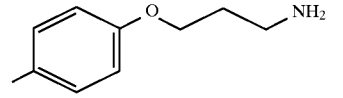 | m.p. 104 to 105 °C. |
| 18 | 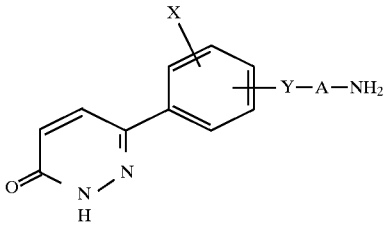 | m.p. 198 to 199 °C. |

Example 19

In 200 ml of acetic acid was suspended 15.00 g of 6-[4-(4-aminobutyl)phenyl]-4,5-dihydropyridazin-3(2H)-one. To the suspension were added 100 ml of a 25% hydrogen bromide-acetic acid solution and then 5.35 g of dimethylsulfoxide, and the mixture was stirred at room temperature for 4.5 hours. 400 ml of isopropyl ether was added to the reaction mixture, and precipitated crystal was collected by filtration and recrystallized from methanol to obtain 18.94 g of 6-[4-(4-aminobutyl)phenyl]pyridazin-3(2H)-one hydrobromide.

m.p.: 271° to 273° C. (decomposed)

Examples 20 to 29

By treating corresponding starting compounds in the same manner as in Example 19, compounds shown in Table 13 were obtained.

TABLE 13

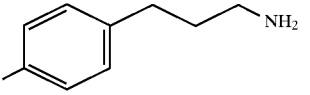

| Example No. | X, Y-A-NH2 | Physcal properties |
|---|---|---|
| 20 |  | m.p. 287 to 289 °C. (decomposed) (hydrobromide) |

TABLE 13-continued

| | | |
|---|---|---|
| 21 | [4-methylphenyl-CH2-CH(CH3)-CH2-CH2-NH2] | m.p. 269 to 270 °C. (hydrochloride) |
| 22 | [4-methylphenyl-CH2-CH(CH2CH3)-CH2-CH2-NH2] | m.p. 189 to 190 °C. (decomposed) (hydrobromide) |
| 23 | [4-methylphenyl-(CH2)5NH2] | m.p. 273 to 275 °C. (decomposed) (hydrobromide) |
| 24 | [4-methyl-3-chlorophenyl-(CH2)4-NH2] | m.p. 237 to 239 °C. (decomposed) (hydrobromide) |

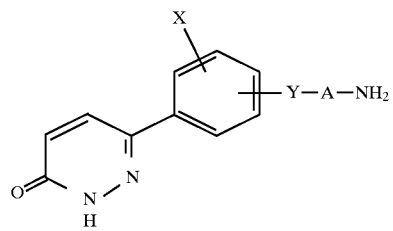

| Example No. | X [phenyl with Y—A—NH2] | Physical properties |
|---|---|---|
| 25 | 4-methyl-3-methoxyphenyl-(CH2)4-NH2 | m.p. 118 to 120 °C. |
| 26 | 4-chloro-2-methylphenyl-(CH2)4-NH2 | m.p. 135 to 137 °C. (hydrobromide) |
| 27 | 3-methylphenyl-(CH2)4-NH2 | m.p. 252 to 253 °C. (decomposed) (hydrobromide) |
| 28 | 4-methylphenyl-O-(CH2)3-NH2 | m.p. 282 to 284 °C. (hydrobromide) |
| 29 | 2-methylphenyl-(CH2)4-NH2 | m.p. 245 to 247 °C. (hydrobromide) |

Example 30

Under ice cooling, a dimethylformamide solution (10 ml) containing 1.06 g of diethylphosphoric cyanide was added dropwise to a dimethylformamide suspension (30 ml) containing 1.65 g of 6-[4-(4-aminobutyl)phenyl]pyridazin-3 (2H)-one hydrobromide, 0.78 g of nicotinic acid and 1.55 g of triethylamine, and the mixture was stirred for 1 hour. The reaction mixture was poured into ice water, and precipitated crystal was collected by filtration. The obtained crystal was washed with water, dried and then recrystallized from methanol to obtain 1.11 g of 6-[4-(4-(pyridin-3-ylcarbonylamino)butyl)phenyl]pyridazin-3(2H)-one.

m.p.: 190° to 191° C.

Examples 31 to 47

By treating corresponding starting compounds in the same manner as in Example 30, compounds shown in Tables 14 to 16 were obtained.

TABLE 14

[Structure: pyridazinone-phenyl-Y-A-N(R¹)-CO-R²]

| Example No. | —Y—A— | R¹ | R² | Physical properties |
|---|---|---|---|---|
| 31 | —(CH₂)₃— | H | 3-pyridyl | m.p. 189 to 190° C. |
| 32 | —(CH₂)₄— | H | 2-methyl-3-pyridyl | m.p. 161 to 163° C. |
| 33 | —(CH₂)₄— | H | 2-amino-3-pyridyl | m.p. 188 to 189° C. |
| 34 | —CH₂CH(CH₃)—(CH₂)₂— | H | 3-pyridyl | m.p. 166 to 167° C. |
| 35 | —CH₂CH(CH₂CH₃)—(CH₂)₂— | H | 3-pyridyl | m.p. 208 to 210° C. (hydrochloride) |
| 36 | —O—(CH₂)₃— | H | 3-pyridyl | m.p. 229 to 231° C. |
| 37 | —(CH₂)₅— | H | 3-pyridyl | m.p. 169 to 170° C. |
| 38 | —(CH₂)₄— | H | 4-pyridyl | m.p. 197 to 198° C. |
| 39 | —(CH₂)₄— | H | pyrazinyl | m.p. 216 to 217° C. |
| 40 | —(CH₂)₄— | H | 1H-pyrrol-3-yl | m.p. 258 to 259° C. |
| 41 | —(CH₂)₄— | —C₂H₅ | | m.p. 125 to 127° C. |

TABLE 15

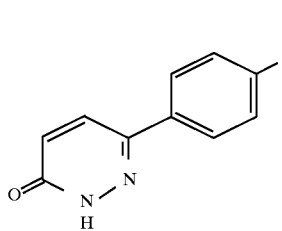

| Example No. | X | Physical properties |
|---|---|---|
| 43 | Cl | m.p. 161 to 162° C. |
| 44 | —OCH₃ | m.p. 138 to 139° C. |
| 45 | H | m.p. 129 to 130° C. |

TABLE 16

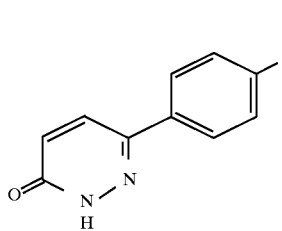

| Example No. | X | Physical properties |
|---|---|---|
| 46 | H | m.p. 147 to 148° C. |
| 47 | Cl | m.p. 164 to 165° C. |

Example 48

An aqueous solution (25 ml) containing 4.30 g of anhydrous potassium carbonate was added to a suspension in which 2.01 g of 6-[4-(4-aminobutyl)phenyl]pyridazin-3(2H)-one hydrobromide was suspended in ethyl acetate (40 ml) and tetrahydrofuran (10 ml). Under ice cooling, 2.23 g of nicotinic acid chloride hydrochloride was added thereto, and the mixture was stirred for 3 hours. Precipitated crystal was collected by filtration, washed with water, dried and then recrystallized from methanol to obtain 1.30 g of 6-[4-(4-(pyridin-3-ylcarbonylamino)butyl)phenyl]pyridazin-3(2H)-one.

m.p.: coincident with that of the compound of Example 30

Examples 49 to 51

By treating corresponding starting compounds in the same manner as in Example 48, compounds shown in Table 17 were obtained.

TABLE 17

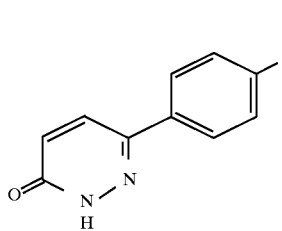

| Example No. | —A— | R¹ | R² | Physical properties |
|---|---|---|---|---|
| 49 | —(CH₂)₃— | H | —CH=CH₂ | m.p. 195 to 196° C. |
| 50 | —(CH₂)₄— | H | 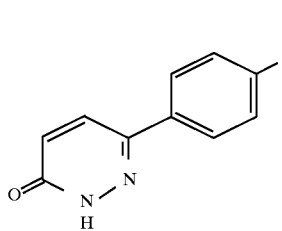 | coincident with that of the compound of Example 38 |
| 51 | —(CH₂)₄— | —C₂H₅ | 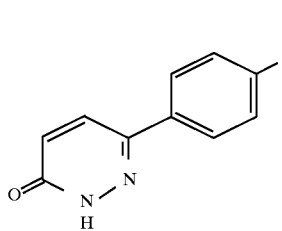 | coincident with that of the compound of Example 41 |

Example 52

(1) 7.50 g of triethylamine was added to a 1,3-dimethyl-2-imidazolidinone suspension (75 ml) containing 7.51 g of 6-[4-(3-aminopropyl)phenyl]-4,5-dihydropyridazin-3(2H)-one, and the mixture was stirred at room temperature for 10 minutes. Then, a tetrahydrofuran solution (40 ml) containing 5.85 g of chloroethylsulfonyl chloride was added to the mixture, and the resulting mixture was stirred at room temperature for 1 hour. The reaction mixture was poured into ice water, and precipitated crystal was collected by filtration and recrystallized from acetonitrile to obtain 5.39 g of 6-[4-(3-vinylsulfonylaminopropyl)phenyl]-4,5-dihydropyridazin-3(2H)-one.

m.p.: 133° to 135° C.

(2) 1.7 g of dimethylsulfoxide was added to a 25% hydrogen bromide-acetic acid suspension (50 ml) containing 5.30 g of 6-[4-(3-vinylsulfonylaminopropyl)phenyl]-4,5-dihydropyridazin-3(2H)-one, and the mixture was stirred at room temperature for 4.5 hours. After hydrogen bromide and acetic acid were removed, a 15% aqueous sodium methyl mercaptide solution (100 ml) was added to the residue, and the mixture was stirred at 60° C. for 1.5 hours. After cooling, the mixture was neutralized with hydrochloric acid, and crystal was collected by filtration, washed with water, dried and then recrystallized from acetonitrile to obtain 3.90 g of 6-[4-(3-(2-methylthioethyl)sulfonylaminopropyl)phenyl]pyridazin-3(2H)-one.

m.p.: 173° to 174° C.

(3) An aqueous solution (25 ml) containing 3.20 g of sodium metaperiodate was added dropwise to an acetic acid suspension (100 ml) containing 5.36 g of 6-[4-(3-(2-methylthioethyl)sulfonylaminopropyl)phenyl]pyridazin-3(2H)-one, and the mixture was stirred at room temperature for 1.5 hours. The reaction mixture was poured into ice water, and precipitated crystal was collected by filtration and dried to obtain 5.00 g of 6-[4-(3-(2-methylsulfinylethyl)sulfonylaminopropyl)phenyl]pyridazin-3(2H)-one.

m.p.: 176° to 177° C.

(4) An ethylene glycol solution (25 ml) containing 2.48 g of 6-[4-(3-(2-methylsulfinylethyl)sulfonylaminopropyl)

phenyl]pyridazin-3(2H)-one was stirred at 180° C. for 1 hour. The reaction mixture was poured into ice water, and precipitated crystal was collected by filtration, washed with water, dried and then recrystallized from methanol to obtain 1.60 g of 6-[4-(3-vinylsulfonylaminopropyl)phenyl]-pyridazin-3(2H)-one.

m.p.: 166° to 168° C.

Example 53

3.54 g of triethylamine was added to a 1,3-dimethyl-2-imidazolidinone suspension (35 ml) containing 3.10 g of 6-[4-(3-aminopropyl)phenyl]pyridazin-3(2H)-one hydrobromide. Then, a tetrahydrofuran solution (15 ml) containing 1.95 g of chloroethylsulfonyl chloride was added to the mixture, and the resulting mixture was stirred at room temperature for 5 hours. The reaction mixture was poured into ice water and extracted with chloroform. After the chloroform layer was washed with water and dried, the solvent was removed. The residue was purified by silica gel column chromatography (eluent: chloroform-methanol (10:1)) to obtain 1.19 g of 6-[4-(3-vinylsulfonylaminopropyl)phenyl]-pyridazin-3(2H)-one.

m.p.: coincident with that of the compound of Example 52-(4)

Example 54

276 mg of triethylamine was added to a dichloromethane suspension (4 ml) containing 100 mg of 6-[4-(3-aminopropoxy)phenyl]pyridazin-3(2H)-one hydrobromide and 37 mg of dimethylaniline, and the mixture was stirred at room temperature for 30 minutes. Under ice cooling, 86 mg of trimethylchlorosilane was added thereto, and the mixture was stirred at room temperature for 2 hours. Again, under ice cooling, a dichloromethane solution (1 ml) containing 65 mg of chloroethylsulfonyl chloride was added dropwise to the mixture, and the resulting mixture was stirred at room temperature for 30 minutes. 5 ml of 1M hydrochloric acid was added to the mixture, and the organic layer was collected by separation. After the organic layer was washed with water and dried, the solvent was removed. The residue was purified by silica gel column chromatography (eluent: chloroform-methanol (30:1)) to obtain 73 mg of 6-[4-(3-vinylsulfonylaminopropoxy)phenyl]pyridazin-3(2H)-one.

m.p.: 197° to 198° C.

Examples 55 to 63

By treating corresponding starting compounds in the same manner as in Example 54, compounds shown in Table 18 were obtained.

TABLE 18

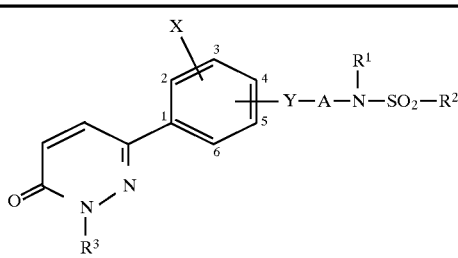

| Example No. | —Y—A— | X | $R^1$ | $R^2$ | $R^3$ | Physical properties |
|---|---|---|---|---|---|---|
| 55 | 4- —$(CH_2)_4$— | H | H | —CH=$CH_2$ | H | m.p. 176 to 178° C. |
| 56 | 4- —$(CH_2)_5$— | H | H | n-$C_3H_7$— | H | m.p. 144 to 145° C. |
| 57 | 4- —$(CH_2)_5$— | H | H | —CH=$CH_2$ | H | m.p. 132 to 133° C. |
| 58 | 4- —$(CH_2)_4$— | H | —$C_2H_5$ | —CH=$CH_2$ | H | m.p. 130 to 131° C. |
| 59 | 5- —$(CH_2)_4$— | 2-$OCH_3$ | H | —CH=$CH_2$ | H | m.p. 115 to 116° C. |
| 60 | 5- —$(CH_2)_4$— | 2-Cl | H | —CH=$CH_2$ | H | m.p. 91 to 92° C. |
| 61 | 3- —$(CH_2)_4$— | H | H | —CH=$CH_2$ | H | m.p. 136 to 137° C. |
| 62 | 2- —$(CH_2)_4$— | H | H | —CH=$CH_2$ | H | m.p. 106 to 107° C. |
| 63 | 2- —$(CH_2)_4$— | 5-Cl | H | —CH=$CH_2$ | H | m.p. 118 to 120° C. |

Example 64

(1) By treating 6-[4-(5-aminopentyl)phenyl]-4,5-dihydropyridazin-3(2H)-one and nicotinic acid in the same manner as in Example 30, 6-[4-(5-(pyridin-3-ylcarbonylamino)pentyl)phenyl]-4,5-dihydropyridazin-3(2H)-one was obtained.

m.p.: 133° to 134° C.

(2) By treating 6-[4-(5-(pyridin-3-ylcarbonylamino)pentyl)phenyl]-4,5-dihydropyridazin-3(2H)-one in the same manner as in Example 19, 6-[4-(5-(pyridin-3-ylcarbonylamino)pentyl)phenyl]pyridazin-3(2H)-one was obtained.

m.p.: coincident with that of the compound of Example 37

Example 65

1.0 g of 10% palladium carbon (Pd/C) and 9.0 g of ammonium formate were added to a methanol solution (100 ml) containing 2.0 g of 6-[2-chloro-5-(4-aminobutyl)phenyl]-4,5-dihydropyridazin-3(2H)-one. The resulting suspension was refluxed under heating for 12 hours. The suspension was left to stand for cooling and then filtered, and the filtrate was removed. The residue was purified by silica gel column chromatography (eluent: chloroform-methanol-28% aqueous ammonia (50:10:1)) to obtain 1.3 g of 6-[5-(4-aminobutyl)phenyl]-4,5-dihydropyridazin-3(2H)-one.

m.p.: 128° to 130° C.

Example 66

By treating 6-[3-chloro-6-(4-aminobutyl)phenyl]-4,5-dihydropyridazin-3(2H)-one in the same manner as in Example 65, 6-[6-(4-aminobutyl)phenyl]-4,5-dihydropyridazin-3(2H)-one was obtained.

m.p.: 78° to 80° C.

Example 67

(1) At an inner temperature of 0° C., 50 g of anhydrous potassium carbonate and then 8.5 g of nicotinic acid chloride hydrochloride were added to a N,N-dimethylacetamide suspension (270 ml) containing 9.0 g of 6-[4-(4-aminobutyl) phenyl]-4,5-dihydropyridazin-3(2H)-one. The reaction mixture was stirred at the same temperature for 30 minutes and then poured into 200 ml of ice water. After the mixture was stirred at room temperature for 2 hours, water (300 ml) was further added to the mixture, and precipitated crystal was collected by filtration. The resulting crystal was washed with water and then recrystallized from methanol to obtain 10.3 g of 6-[4-(4-(pyridin-3-ylcarbonylamino)butyl)phenyl]-4,5-dihydropyridazin-3(2H)-one.

m.p.: 178° to 179° C.

(2) In acetic acid (100 ml) was dissolved 10.0 g of 6-[4-(4-(pyridin-3-ylcarbonylamino)butyl)phenyl]-4,5-dihydropyridazin-3(2H)-one. 25% hydrogen bromide-acetic acid (100 ml) was added to the solution, and the mixture was stirred at room temperature for 5 minutes. 2.9 g of dimethylsulfoxide was added to the mixture at room temperature, and the resulting mixture was stirred at the same temperature for 1 hour. Ethanol (150 ml) was added to the reaction mixture, and the mixture was stirred for 2 hours. Diisopropyl ether (150 ml) was further added to the mixture, and the resulting mixture was stirred for 2 hours. Precipitated crystal was collected by filtration, washed with diisopropyl ether and then dissolved in hydrated ethanol, and the solution was neutralized with aqueous ammonia. Precipitated crystal was collected by filtration, washed with water and then recrystallized from methanol to obtain 8.9 g of 6-[4-(4-(pyridin-3-ylcarbonylamino)butyl)phenyl]pyridazin-3(2H)-one.

m.p.: coincident with that of the compound of Example 30

Example 68

(1) By treating a corresponding starting compound in the same manner as in Example 67-(1), 6-[4-(3-(pyridin-3-ylcarbonylamino)propoxy)phenyl]-4,5-dihydropyridazin-3(2H)-one was obtained.

m.p.: 197° to 198° C.

(2) By treating 6-[4-(3-(pyridin-3-ylcarbonylamino) propoxy)phenyl]-4,5-dihydropyridazin-3(2H)-one in the same manner as in Example 67-(2), 6-[4-(3-(pyridin-3-ylcarbonylamino)propoxy)phenyl]pyridazin-3(2H)-one was obtained.

m.p.: coincident with that of the compound of Example 36

Example 69

In hot ethanol (180 ml) was dissolved 8.9 g of 6-[4-(4-(pyridin-3-ylcarbonylamino)butyl)phenyl]pyridazin-3(2H)-one. A 18% hydrochloric acid-ethanol solution (10 ml) was added to the solution, and the mixture was left to stand at room temperature. Precipitated crystal was collected by filtration and washed with cold ethanol to obtain 9.3 g of 6-[4-(4-(pyridin-3-ylcarbonylamino)butyl)phenyl] pyridazin-3(2H)-one hydrochloride.

m.p.: 245° to 247° C. (recrystallized from ethanol) chloride monohydrate m.p.: 240° to 243° C. (recrystallized from aqueous ethanol)

Examples 70 to 73

By treating corresponding starting compounds in the same manner as in Example 69, compounds shown in Table 19 were obtained.

TABLE 19

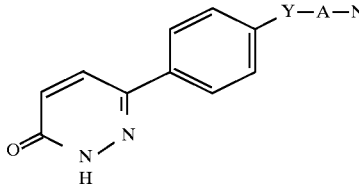

| Example No. | —Y—A— | $R^2$ | Physical properties |
|---|---|---|---|
| 70 | —(CH$_2$)$_4$— | 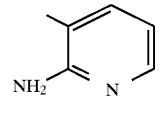 | m.p. 257 to 259° C. |
| 71 | —O—(CH$_2$)$_3$— | 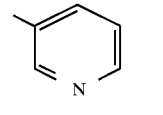 | m.p. 257 to 258° C. |
| 72 | —O—(CH$_2$)$_3$— | 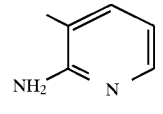 | m.p. 268 to 270° C. |
| 73 | —O—(CH$_2$)$_4$— | 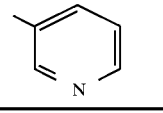 | m.p. 217 to 219° C. |

Example 74

868 mg of nicotinic acid, 954 mg of N-hydroxybenzotriazole and triethylamine (1.23 ml) were added to a dimethylformamide solution (50 ml) containing 2.0 g of 6-[4-(4-aminobutoxy)phenyl]pyridazin-3(2H)-one hydrobromide. 1.35 g of 1-ethyl-3-(3'-dimethylaminopropyl)carbodiimide was added to the mixture at 0° C., and the resulting mixture was stirred at room temperature for 6 hours and then poured into ice water, and precipitated crystal was collected by filtration. The crystal was recrystallized from ethanol to obtain 1.75 g of 6-[4-(4-(pyridin-3-ylcarbonylamino)butoxy)phenyl]pyridazin-3 (2H)-one.

m.p.: 155° to 157° C.

Example 75

By treating a corresponding starting compound in the same manner as in Example 74, 6-[4-(6-(pyridin-3-ylcarbonylamino)hexyl)phenyl]pyridazin-3(2H)-one was obtained.

m.p.: 178° to 179° C.

Example 76

By reacting a corresponding starting compound with 2-aminonicotinic acid in the same manner as in Example 74, 6-[4-(3-(2-aminopyridin-3-ylcarbonylamino)propoxy) phenylpyridazin-3(2H)-one was obtained.

m.p.: 232° to 234° C.

Example 77

(1) By treating a corresponding starting compound in the same manner as in Example 11, 4-(4-phthalimidobutoxy)-1-(3-hydroxycarbonylpropionyl)benzene was obtained.

m.p.: 133° to 134° C.

(2) By treating 4-(4-phthalimidobutoxy)-1-(3-hydroxycarbonylpropionyl)benzene in the same manner as in Example 15, 6-[4-(4-aminobutoxy)phenyl]-4,5-dihydropyridazin-3(2H)-one was obtained.

m.p.: 191° to 192° C.

(3) By treating 6-[4-(4-aminobutoxy)phenyl]-4,5-dihydropyridazin-3(2H)-one in the same manner as in Example 19, 6-(4-(4-aminobutoxy)phenyl]pyridazin-3(2H)-one hydrobromide was obtained.

m.p.: 247° to 250° C.

Example 78

(1) By treating a corresponding starting compound in the same manner as in Example 1, 4-[6-(acetylamino)hexyl]-1-(3-methoxycarbonylpropionyl)benzene was obtained.

m.p.: 87° to 89° C.

(2) By treating 4-[6-(acetylamino)hexyl]-1-(3-methoxycarbonylpropionyl)benzene in the same manner as in Example 6, 6-[4-(6-aminohexyl)phenyl]-4,5-dihydropyridazin-3(2H)-one was obtained.

m.p.: 153° to 154° C.

(3) By treating 6-[4-(6-aminohexyl)phenyl]-4,5-dihydropyridazin-3(2H)-one in the same manner as in Example 19, 6-[4-(6-aminohexyl)phenyl]pyridazin-3(2H)-one hydrobromide was obtained.

m.p.: 251° to 253° C.

Example 79

(1) Under ice cooling, 20.9 g of anhydrous aluminum chloride was added to 200 ml of a dichloroethane solution containing 10.0 g of [4-(acetylamino)butyl]benzene and 9.96 g of 2-chloropropionyl chloride, and the mixture was stirred at 5° C. for 1 hour. The reaction mixture was poured into ice water, and the organic layer was collected by separation. After the organic layer was washed with water and dried, the solvent was removed to obtain 13.71 g of 4-[4-(acetylamino)butyl]-1-(2-chloropropionyl)benzene.

m.p.: 66° to 67° C.

(2) 27.90 g of malonic acid di(tert-butyl) ester was added dropwise to 300 ml of a dimethylformamide suspension containing 5.17 g of 60% sodium hydride, and the mixture was stirred at room temperature overnight. Under ice cooling, 100 ml of a dimethylformamide solution containing 24.2 g of 4-[4-(acetylamino)butyl]-1-(2-chloropropionyl)benzene was added dropwise to the reaction mixture. The resulting mixture was stirred at room temperature for 1 hour and further stirred at 50° C. for 1 hour. The reaction mixture was poured into ice water and extracted with chloroform. After the chloroform layer was washed with water and dried, the solvent was removed to obtain 35.21 g of 4-[4-(acetylamino)butyl]-1-{[3,3-di(tert-butoxycarbonyl)-2-methyl]propionyl} benzene as an oily material.

(3) 70 ml of trifluoroacetic acid was added to 600 ml of a dichloromethane solution containing 35.21 g of 4-[4-(acetylamino)butyl]-1-{[3,3-di(tert-butoxycarbonyl)-2-methyl]propionyl}benzene. The mixture was stirred at room temperature for 1.5 hours and then refluxed under heating for 3 hours. After removal of the solvent, 400 ml of acetic acid was added to the residue and the mixture was refluxed for 3 hours. The acetic acid was removed to obtain 19.60 g of 4-[4-(acetylamino)butyl]-1-[(3-hydroxycarbonyl-2-methyl)propionyl]benzene.

IR (neat) cm$^{-1}$: 1720, 1680, 1610

MS (ESI) m/z: 323 (M+NH$_4$)

(4) In 24 ml of 10M hydrochloric acid was suspended 760 mg of 4-[4-(acetylamino)butyl]-1-[(3-hydroxycarbonyl-2-methyl)propionyl]benzene, and the suspension was refluxed under heating overnight. After concentration, the residue was dissolved in 15 ml of acetic acid. 880 mg of hydrazine monohydrate was added to the solution, and the mixture was refluxed under heating for 18 hours. Acetic acid was removed, and the residue was dissolved in water. The solution was made alkaline with ammonia and extracted with chloroform. After the chloroform layer was washed with water and dried, the solvent was removed. The resulting crude crystal was recrystallized from ethyl acetate to obtain 421 mg of 6-[4-(4-aminobutyl)phenyl]-4,5-dihydro-5-methylpyridazin-3(2H)-one.

m.p.: 135° to 137° C.

Example 80

(1) By treating [3-(phthalimido)propoxy]benzene and 2-chloropropionyl chloride in the same manner as in Example 79-(1), 4-[3-(phthalimido)propoxy]-1-(2-chloropropionyl)benzene was obtained.

m.p.: 137° to 138° C.

(2) By treating 4-[3-(phthalimido)propoxy]-1-(2-chloropropionyl)benzene and malonic acid di(tert-butyl) ester in the same manner as in Example 79-(2), 4-[3-(phthalimido)propoxy]- 1-{[3,3-di(tert-butoxycarbonyl)-2-methyl]propionyl}benzene was obtained.

m.p.: 103° to 105° C.

(3) By treating 4-[3-(phthalimido)propoxy]-1-{[3,3-di(tert-butoxycarbonyl)-2-methyl]propionyl}benzene in the same manner as in Example 79-(3), 4-[3-(phthalimido)propoxy]-1-[(3-hydroxycarbonyl-2-methyl)propionyl]benzene was obtained.

m.p.: 122° to 123° C.

(4) 6.50 g of hydrazine monohydrate was added to 200 ml of an ethanol suspension containing 10.0 g of 4-[3-(phthalimido)propoxy]-1-[(3-hydroxycarbonyl-2-methyl)propionyl]-benzene, and the mixture was refluxed under heating for 5 hours. Ethanol was removed, and the residue was dissolved in chloroform. After the chloroform layer was washed with water and dried, the solvent was removed to obtain 6.61 g of 6-[4-(3-aminopropoxy)phenyl]-4,5-dihydro-5-methyl-pyridazin-3(2H)-one.

m.p.: 136° to 138° C.

Example 81

(1) Under ice cooling, 1.64 g of anhydrous aluminum chloride was added to 18 ml of a dichloroethane solution containing 590 mg of [4-(acetylamino)butyl]benzene and 790 mg of 2,3-dimethylsuccinic anhydride, and the mixture was stirred for 1 hour. The reaction mixture was poured into ice water and extracted with chloroform. After the chloroform layer was washed with water and dried, the solvent was removed. The residue was purified by silica gel column chromatography (eluent: chloroform-methanol (4:1)) to obtain 960 mg of 4-[4-(acetylamino)butyl]-1-[(3-hydroxycarbonyl-2,3-dimethyl)propionyl]benzene.

IR (neat) cm$^{-1}$: 1710, 1680, 1610

MS (ESI) m/z: 337 (M+NH$_4$)

(2) 80 ml of hydrazine monohydrate was added to 4.02 g of 4-[4-(acetylamino)butyl]-1-[(3-hydroxycarbonyl-2,3-dimethyl)propionyl]benzene, and the mixture was refluxed under heating for 4 hours. The reaction mixture was poured into ice water and extracted with ethyl acetate. After the ethyl acetate layer was washed with water and dried, the solvent was removed. The residue was purified by silica gel column chromatography (eluent: chloroform-methanol-28% aqueous ammonia (10:1:0.1)) to obtain 2.09 g of 6-[4-(4-aminobutyl)phenyl]-4,5-dihydro-4,5-dimethylpyridazin-3 (2H)-one.

IR (neat) cm$^{-1}$: 1680

MS (ESI) m/z: 278 (MH)$^+$ (3) 44 ml of a 25% hydrogen bromide-acetic acid solution was added to 44 ml of an acetic acid solution containing 2.20 g of 6-[4-(4-aminobutyl)phenyl]-4,5-dihydro-4,5-dimethylpyridazin-3(2H)-one, and the mixture was stirred at room temperature for 5 minutes. Then, 0.75 ml of dimethylsulfoxide was added to the mixture, and the resulting mixture was stirred for 6 hours. The solvent was removed, and the residue was dissolved in 150 ml of water. The solution was made alkaline with ammonia and extracted with chloroform. After the chloroform layer was washed with water and dried, the solvent was removed. The residue was purified by silica gel column chromatography (eluent: chloroform-methanol-28% aqueous ammonia (10:1:0.1)) to obtain 1.52 g of 6-[4-(4-aminobutyl)phenyl]-4,5-dimethylpyridazin-3(2H)-one.

m.p.: 162° to 163° C.

Example 82

(1) By treating [4-(acetylamino)butyl]benzene and crotonoyl chloride in the same manner as in Example 79-(1), 4-[4-(acetylamino)butyl]-1-(2-butenoyl)benzene was obtained.

m.p. 64° to 66° C.

(2) 1.1 ml of a 10% sodium carbonate aqueous solution was added to 15 ml of a methanol solution containing 510 mg of 4-(4-acetylamino)butyl]-1-(2-butenoyl)benzene and 1.69 g of acetocyanhydrin, and the mixture was refluxed under heating for 2 hours. The solvent was removed, and the residue was purified by silica gel column chromatography (eluent: chloroform-methanol (40:1)) to obtain 450 mg of 4-[4-(acetylamino)butyl]-1-(3-cyanobutanoyl)benzene.

m.p.: 89° to 90° C.

(3) 7.50 g of 4-[4-(acetylamino)butyl]-1-(3-cyanobutanoyl)benzene was suspended in 180 ml of 10M hydrochloric acid, and the suspension was refluxed under heating overnight. The reaction mixture was concentrated to a half amount, and precipitated crystal was collected by filtration. After the crystal was dissolved in 110 ml of acetic acid, 5.29 g of hydrazine monohydrate was added to the solution, and the mixture was refluxed under heating for 4 hours. Acetic acid was removed, and the residue was dissolved in water. The solution was made alkaline with ammonia and left to stand overnight. Precipitated crystal was collected by filtration, washed with water, dried and then recrystallized from ethyl acetate-methanol to obtain 4.23 g of 6-[4-(4-aminobutyl)phenyl]-4,5-dihydro-4-methylpyridazin-3(2H)-one.

m.p.: 118° to 120° C.

Example 83

(1) By treating [3-(4-phthalimidobutyl)-4-methyl]chlorobenzene and succinic anhydride in the same manner as in Example 11, [5-(4-phthalimidobutyl)-2-(3-hydroxycarbonylpropionyl)-4-methyl]chlorobenzene was obtained.

m.p.: 116° to 118° C.

(2) By treating [5-(4-phthalimidobutyl)-2-(3-hydroxycarbonylpropionyl)-4-methyl]chlorobenzene and hydrazine monohydrate in the same manner as in Example 15, 6-[2-chloro-5-methyl-4-(4-aminobutyl)phenyl]-4,5-dihydropyridazin-3(2H)-one was obtained.

m.p. 181° to 182° C.

(3) By treating 6-[2-chloro-5-methyl-4-(4-aminobutyl)phenyl]-4,5-dihydropyridazin-3(2H)-one in the same manner as in Example 65, 6-[3-methyl-4-(4-aminobutyl)phenyl]-4,5-dihydropyridazin-3(2H)-one was obtained.

m.p.: 145° to 147° C.

Examples 84 to 86

By treating corresponding starting compounds in the same manner as in Example 67-(1), compounds shown in Table 20 were obtained.

TABLE 20

| Example No | X | —Y—A— | R$^4$ | R$^5$ | Physical properties |
|---|---|---|---|---|---|
| 84 | H | —(CH$_2$)$_4$— | —CH$_3$ | H | m.p. 160 to 161° C. |
| 85 | H | —O—(CH$_2$)$_3$— | —CH$_3$ | H | m.p. 183 to 185° C. |
| 86 | H | —(CH$_2$)$_4$— | H | —CH$_3$ | m.p. 191 to 193° C. |

Example 87

690 mg of nicotinic acid and 760 mg of N-hydroxybenzotriazole were added to 80 ml of a dimethylformamide solution containing 1.39 g of 6-[4-(4-aminobutyl)phenyl]-4,5-dimethylpyridazin-3(2H)-one. Under ice cooling, 1.08 g of 1-ethyl-3-(3'-dimethylaminopropyl)carbodiimide was added thereto, and the mixture was stirred at room temperature for 3 hours. The reaction mixture was poured into ice water, and precipitated crystal was collected by filtration and recrystallized from 2-propanol to obtain 1.41 g of 6-[4-[4-(pyridin-3-ylcarbononylamino)butyl]phenyl]-4,5-dimethylpyridazin-3 (2H)-one.

m.p.: 211° to 212° C.

Example 88

By treating 6-[3-methyl-4-(4-aminobutyl)phenyl]-4,5-dihydropyridazin-3(2H)-one and nicotinic acid in the same manner as in Example 87, 6-[3-methyl-4-[4-(pyridin-3-ylcarbonylamino)butyl]phenyl]- 4,5-dihydropyridazin-3 (2H)-one was obtained.

m.p.: 160° to 161° C.

Example 89

By treating 6-[4-(4-aminobutyl)phenyl]pyridazin-3(2H)-one and pyridazin-4-carboxylic acid in the same manner as in Example 87, 6-[4-[4-(pyridazin-4-ylcarbonylamino) butyl]-phenyl]pyridazin-3(2H)-one was obtained.

m.p.: 183° to 185° C.

Examples 90 to 95

By treating corresponding starting compounds in the same manner as in Example 67-(2), compounds shown in Table 21 were obtained.

TABLE 21

| Example No. | X | —Y—A— | $R^2$ | $R^4$ | $R^5$ | Physical properties |
|---|---|---|---|---|---|---|
| 90 | H | —(CH$_2$)$_4$— | 3-pyridyl | —CH$_3$ | H | m.p. 202 to 203° C. |
| 91 | H | —O—(CH$_2$)$_3$— | 3-pyridyl | —CH$_3$ | H | m.p. 209 to 211° C. |
| 92 | H | —(CH$_2$)$_4$— | 3-pyridyl | H | —CH$_3$ | m.p. 242 to 243° C. |
| 93 | H | —(CH$_2$)$_2$— | 3-pyridyl | —CH$_3$ | H | m.p. 209 to 210° C. |
| 94 | H | —(CH$_2$)$_2$— | 3-pyridyl | H | H | m.p. 232 to 233° C. |
| 95 | —CH$_3$ | —(CH$_2$)$_4$— | 3-pyridyl | H | H | m.p. 175 to 176° C. |

Examples 96 to 102

By treating corresponding starting compounds in the same manner as in Example 69, compounds shown in Table 22 were obtained.

TABLE 22

| Example No. | X | —Y—A— | R² | R⁴ | R⁵ | Physical properties |
|---|---|---|---|---|---|---|
| 96 | H | —(CH₂)₄— | 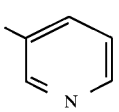 | —CH₃ | H | m.p. 238 to 240° C. |
| 97 | H | —O—(CH₂)₃— | 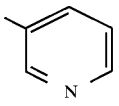 | —CH₃ | H | m.p. 244 to 246° C. |
| 98 | H | —(CH₂)₄— | 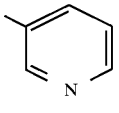 | —CH₃ | —CH₃ | m.p. 258 to 261° C. |
| 99 | H | —(CH₂)₄— | 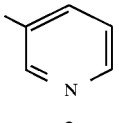 | H | —CH₃ | m.p. 248 to 250° C. |
| 100 | H | —(CH₂)₂— | 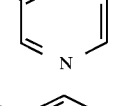 | —CH₃ | H | m.p. 263 to 264° C. |
| 101 | H | —(CH₂)₂— | 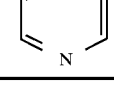 | H | H | m.p. 267 to 270° C. |
| 102 | —CH₃ | —(CH₂)₄— |  | H | H | m.p. 243 to 245° C. |

Example 103

By treating 6-[4-(4-aminobutyl)phenyl]pyridazin-3(2H)-one and 3-ethyl-5-carboxyisoxazole in the same manner as in Example 87, 6-{4-[4-(3-methylisoxazole-5-ylcarbonylamino) butyl]phenyl}pyridazin-3(2H)-one was obtained.

36° to 238° C.

The pyridazinone derivative (I) and a pharmaceutically acceptable salt thereof which are the desired compounds of the present invention have excellent antinephritic actions and/or excellent actions of protecting from endotoxin shock. Therefore, the desired compounds of the present invention are useful as an agent for preventing and treating nephritis (e.g., glomerular nephritis (immunoglobulin A nephropathy, nephrotic syndrome, lupus nephritis and the like)) and/or an agent for preventing renal insufficiency. Also, the desired compounds of the present invention are useful as an agent for preventing and treating endotoxin shock which occurs in a patient seriously infected with gram-negative bacteria.

The desired compound (I) of the present invention has low toxicity. For example, when 6-[4-(4-(pyridin-3-ylcarbonylamino)butyl)phenyl]pyridazin-3(2H)-one hydrochloride was administered orally to mice in a dose of 1,000 mg/kg and the mice were observed for 3 days or when said compound was administered intraperitoneally to mice in a dose of 300 mg/kg and the mice were observed for 3 days, no case of death was observed.

Further, the desired compound (I) of the present invention exhibits excellent pharmaceutical effects as described above and also has extremely less side effect to a circulatory system so that it can be a medicine having high safety.

We claim:

1. A process for preparing a pyridazinone compound represented by the formula (I-a):

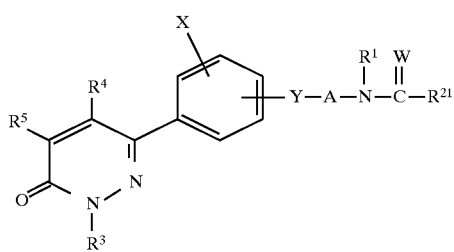

(I-a)

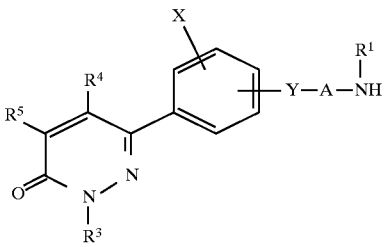

(II)

wherein W represents oxygen atom; $R^{21}$ represents a monocyclic heterocyclic aromatic group which has a nitrogen atom, and may have a substituent(s); X represents hydrogen atom, a lower alkyl group which may have a substituent(s), a lower alkoxy group, carboxy group, an alkoxycarbonyl group, nitro group, cyano group, a lower alkylthio group, hydroxy group, an amino group which may have a substituent (s), or a halogen atom; Y represents a single bonding arm, oxygen atom or sulfur atom; A represents a straight or branched alkylene group which may have a double bond;

$R^1$ represents hydrogen atom, a lower alkyl group which may be substituted or a lower alkenyl group; $R^3$ represents hydrogen atom or a lower alkyl group which may be substituted;

$R^4$ represents hydrogen atom or a lower alkyl group; and $R^5$ represents hydrogen atom or a lower alkyl group, or a pharmaceutically acceptable salt thereof, which comprises reacting a pyridazinone compound represented by the formula (II):

wherein X, Y, A, $R^1$, $R^3$, $R^4$ and $R^5$ have the same meanings as defined above, or a salt thereof with a compound represented by the formula (III):

(III)

wherein W and $R^{21}$ have the same meanings as defined above, a reactive derivative thereof or a salt thereof, and, if necessary, converting the resulting compound into a pharmaceutically acceptable salt thereof.

* * * * *